United States Patent
Hyun et al.

(10) Patent No.: US 10,695,033 B2
(45) Date of Patent: Jun. 30, 2020

(54) ULTRASOUND DIAGNOSTIC APPARATUS AND METHOD OF OPERATING THE SAME

(71) Applicant: SAMSUNG MEDISON CO., LTD., Hongcheon-gun (KR)

(72) Inventors: Dong-gyu Hyun, Hongcheon-gun (KR); Dong-hoon Oh, Hongcheon-gun (KR); Jae-heung Yoo, Seoul (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 1289 days.

(21) Appl. No.: 14/887,883

(22) Filed: Oct. 20, 2015

(65) Prior Publication Data

US 2016/0166236 A1 Jun. 16, 2016

(30) Foreign Application Priority Data

Dec. 11, 2014 (KR) .......................... 10-2014-0178706

(51) Int. Cl.
*A61B 8/06* (2006.01)
*A61B 8/00* (2006.01)
*A61B 8/08* (2006.01)

(52) U.S. Cl.
CPC .............. *A61B 8/5207* (2013.01); *A61B 8/06* (2013.01); *A61B 8/483* (2013.01); *A61B 8/5246* (2013.01);
(Continued)

(58) Field of Classification Search
CPC ......... A61B 8/5207; A61B 8/06; A61B 8/443; A61B 8/463; A61B 8/481; A61B 8/488; A61B 8/485; A61B 8/469; A61B 8/523; A61B 8/5246; A61B 8/0891; A61B 8/00; A61B 8/08; Y10S 128/916
See application file for complete search history.

(56) References Cited

U.S. PATENT DOCUMENTS 6,251,072 B1 6/2001 Ladak et al.
6,599,244 B1 7/2003 Epps et al.
(Continued)

FOREIGN PATENT DOCUMENTS

JP 4071101 B2 4/2008
JP 2010-094274 A 4/2010
(Continued)

OTHER PUBLICATIONS

International Search Report in PCT/KR2015/006923, dated Sep. 30, 2015.
(Continued)

*Primary Examiner* — Boniface N Nganga
(74) *Attorney, Agent, or Firm* — Sughrue Mion, PLLC

(57) ABSTRACT

Disclosed is an ultrasound diagnostic method for an object having a tubular shape. The ultrasound diagnostic method includes acquiring ultrasound volume data of the object, generating a first ultrasound image which is obtained by imaging a surface of the object, based on the ultrasound volume data, generating a second ultrasound image which is obtained by imaging at least one selected from blood flow, stiffness, a thickness of a wall, and contrast agent augmentation of an inside of the object included in the first ultrasound image, based on the ultrasound volume data, and displaying the first ultrasound image and the second ultrasound image.

12 Claims, 19 Drawing Sheets

(52) U.S. Cl.
CPC ............ *A61B 8/0891* (2013.01); *A61B 8/463* (2013.01); *A61B 8/469* (2013.01); *A61B 8/481* (2013.01); *A61B 8/485* (2013.01); *A61B 8/488* (2013.01); *A61B 8/523* (2013.01)

(56) References Cited

U.S. PATENT DOCUMENTS

| | | | |
|---|---|---|---|
| 6,599,248 B1* | 7/2003 | Tamura | A61B 8/06 600/454 |
| 7,742,629 B2 | 6/2010 | Zarkh et al. | |
| 2007/0078343 A1 | 4/2007 | Kawashima et al. | |
| 2007/0129631 A1* | 6/2007 | Ma | A61B 8/06 600/437 |
| 2008/0177182 A1* | 7/2008 | Takimoto | A61B 8/06 600/441 |
| 2011/0206248 A1 | 8/2011 | Ruijters | |
| 2013/0096430 A1 | 4/2013 | Yoshiara et al. | |
| 2013/0194267 A1 | 8/2013 | Tsujita | |
| 2013/0281846 A1 | 10/2013 | Yoshiara et al. | |
| 2014/0015836 A1 | 1/2014 | Neubauer et al. | |
| 2014/0024937 A1 | 1/2014 | Kim et al. | |
| 2014/0031690 A1 | 1/2014 | Toji et al. | |
| 2014/0039317 A1 | 2/2014 | Sato | |
| 2014/0378835 A1* | 12/2014 | Satoh | A61B 8/06 600/441 |
| 2015/0087981 A1* | 3/2015 | Ishii | G06T 19/003 600/440 |

FOREIGN PATENT DOCUMENTS

| | | | |
|---|---|---|---|
| JP | 2010-536412 A | 12/2010 | |
| JP | 5129480 B2 | 1/2013 | |
| JP | 2014-503272 A | 2/2014 | |
| KR | 10-0426396 B1 | 4/2004 | |
| WO | 03/101303 A1 | 12/2003 | |
| WO | WO-2013146716 A1 * | 10/2013 | ............ A61B 8/06 |
| WO | 2014/021402 A1 | 2/2014 | |

OTHER PUBLICATIONS

Written Report of the International Searching Authority in PCT/KR2015/006923, dated Sep. 30, 2015.

Communication dated May 9, 2018, issued by the European Patent Office in counterpart European Application No. 15867470.5.

* cited by examiner

ULTRASOUND DIAGNOSTIC APPARATUS AND METHOD OF OPERATING THE SAME

RELATED APPLICATION

This application claims the benefit of Korean Patent Application No. 10-2014-0178706, filed on Dec. 11, 2014, in the Korean Intellectual Property Office, the disclosure of which is incorporated herein in its entirety by reference.

BACKGROUND

1. Field

One or more exemplary embodiments relate to an ultrasound diagnostic apparatus and a method of operating the same, and more particularly, to an apparatus and a method for an ultrasound diagnosis of a tubular tissue.

2. Description of the Related Art

In an ultrasound system of the related art, a method, which divides a screen into four pieces and shows three axial-direction (an X axis, a Y axis, and a Z axis) plane images and three-dimensionally rendered data, is used for displaying an ultrasound three-dimensional (3D) image.

In detail, a multi-planner view (MPV) method, which shows three axial-direction (an X axis, a Y axis, and a Z axis) planes having orthogonality with respect to an arbitrary origin of a 3D space, is used for displaying anatomical images of a face, a spine, and a brain of a fetus. As another method, a multi-slice view (MSV) method, which shows an arbitrary slice designated by a user, is used.

Moreover, a thickness of each of a surface and a wall which surround an internal center line of an organ is observed for diagnosing tubular organs such as digestive organs (a small intestine, a large intestine, a stomach, an esophagus, and a duodenum).

For example, for Crohn's disease, it is required to check a change in a shape of a wall of a colon and whether the wall swells or bursts and thus a perforation is formed.

However, in the above-described MPV or MSV method, it is difficult to observe a thickness of a wall of a tubular object or a tubular inner wall.

SUMMARY

One or more exemplary embodiments include an ultrasound diagnostic method and apparatus, which enable a user to intuitively know the characteristics of a region of interest (ROI), selected by the user, on a screen.

One or more exemplary embodiments include an ultrasound diagnostic method and apparatus for observing an inner wall of a tubular object and a thickness of the wall.

One or more exemplary embodiments include an ultrasound diagnostic method and apparatus which enable a user to manipulate an image displayed on a screen along a center line instead of an arbitrary point when diagnosing a tubular object.

Additional aspects will be set forth in part in the description which follows and, in part, will be apparent from the description, or may be learned by practice of the presented exemplary embodiments.

According to one or more exemplary embodiments, an ultrasound diagnostic method for an object having a tubular shape includes: acquiring ultrasound volume data of the object; generating a first ultrasound image which is obtained by imaging a surface of the object, based on the ultrasound volume data; generating a second ultrasound image which is obtained by imaging at least one selected from blood flow, stiffness, a thickness of a wall, and contrast agent augmentation of an inside of the object included in the first ultrasound image, based on the ultrasound volume data; and displaying the first ultrasound image and the second ultrasound image at the same time.

The displaying may include displaying the second ultrasound image to overlap the first ultrasound image.

The displaying may include displaying the first ultrasound image and the second ultrasound image to overlap each other through weighted sum.

The generating of the second ultrasound image may include generating at least one selected from a color Doppler image, an elasticity image, and a contrast agent augmentation image of the inside of the object included in the first ultrasound image, based on the ultrasound volume data.

The generating of the first ultrasound image may include generating a virtual endoscope image of the object, based on the ultrasound volume data.

The generating of the first ultrasound image may include generating an image which represents a slice parallel to an axis of the object or an image which represents a slice vertical to the axis, based on the ultrasound volume data.

The displaying may include displaying the first ultrasound image in which a center line, which is formed in an axial direction of the object, is marked.

The generating of the second ultrasound image may include: acquiring distance data which includes at least one selected from a distance from the center line to an inner wall and a distance from the center line to an outer wall; and generating an analysis graph, based on the center line and the distance data.

The displaying may include: displaying the first ultrasound image on a first region of a screen; and displaying the second ultrasound image, corresponding to a region of interest (ROI) selected from the first ultrasound image, on a second region of the screen.

According to one or more exemplary embodiments, an ultrasound diagnostic apparatus an object having a tubular shape includes: an acquirer that acquires ultrasound volume data of the object; a first ultrasound image generator that generates a first ultrasound image which is obtained by imaging a surface of the object, based on the ultrasound volume data; a second ultrasound image generator that generates a second ultrasound image which is obtained by imaging at least one selected from blood flow, stiffness, a thickness of a wall, and contrast agent augmentation of an inside of the object included in the first ultrasound image, based on the ultrasound volume data; and a display that displays the first ultrasound image and the second ultrasound image.

The display may display the second ultrasound image to overlap the first ultrasound image.

The display may display the first ultrasound image and the second ultrasound image to overlap each other through weighted sum.

The second ultrasound image generator may generate at least one selected from a color Doppler image, an elasticity image, and a contrast agent augmentation image of the inside of the object included in the first ultrasound image, based on the ultrasound volume data.

The first ultrasound image generator may generate a virtual endoscope image of the object, based on the ultrasound volume data.

The first ultrasound image generator may generate an image which represents a slice parallel to an axis of the object or an image which represents a slice vertical to the axis, based on the ultrasound volume data.

The display may display the first ultrasound image in which a center line, which is formed in an axial direction of the object, is marked.

The second ultrasound image generator may acquire distance data which includes at least one selected from a distance from the center line to an inner wall and a distance from the center line to an outer wall, and generate an analysis graph, based on the center line and the distance data.

The display may display the first ultrasound image on a first region of a screen, and display the second ultrasound image, corresponding to a region of interest (ROI) selected from the first ultrasound image, on a second region of the screen.

The display may mark a cursor, which is used to set the ROI, on the center line.

The cursor may move along the center line, and the second ultrasound image generator may generate the analysis graph corresponding to the ROI which is set by the cursor, based on the ultrasound volume data.

According to one or more exemplary embodiments, an ultrasound diagnostic method for an object having a tubular shape includes: acquiring ultrasound volume data of the object; generating a first ultrasound image which represents a surface of the object, based on the ultrasound volume data; generating a second ultrasound image which represents at least one selected from a plane corresponding to a surface of an inner wall of the object and a plane corresponding to a surface of an outer wall of the object, based on the ultrasound volume data; and displaying the first ultrasound image, in which a center line which is formed in an axial direction of the object is marked, and the second ultrasound image.

The displaying may include: displaying the first ultrasound image on a first region of a screen; and displaying the second ultrasound image, corresponding to a region of interest (ROI) selected from the first ultrasound image, on a second region of the screen.

According to one or more exemplary embodiments, an ultrasound diagnostic apparatus for an object having a tubular shape includes: an acquirer that acquires ultrasound volume data of the object; a first ultrasound image generator that generates a first ultrasound image which represents a surface of the object, based on the ultrasound volume data; a second ultrasound image generator that generates a second ultrasound image which represents at least one selected from a plane corresponding to a surface of an inner wall of the object and a plane corresponding to a surface of an outer wall of the object, based on the ultrasound volume data; and a display that displays the first ultrasound image, in which a center line which is formed in an axial direction of the object is marked, and the second ultrasound image.

The display may display the first ultrasound image on a first region of a screen, and display the second ultrasound image, corresponding to a region of interest (ROI) selected from the first ultrasound image, on a second region of the screen.

The display may mark a cursor, which is used to set the ROI, on the center line.

The cursor may move along the center line, and the second ultrasound image generator may generate the analysis graph corresponding to the ROI which is set by the cursor, based on the ultrasound volume data.

An abscissa axis of the second ultrasound image may indicate a position on the center line, and an ordinate axis of the second ultrasound image may indicate a rotation angle with respect to the center line.

According to one or more exemplary embodiments, an ultrasound diagnostic method for an object having a tubular shape includes: acquiring ultrasound volume data of the object; acquiring a center line which is formed in a long-axis direction of the object and acquiring distance data which includes at least one selected from a distance from the center line to an inner wall of the object and a distance from the center line to an outer wall of the object, based on the ultrasound volume data; generating an analysis graph, based on the center line and the distance data; and displaying the analysis graph.

The analysis graph may show a result which is obtained by calculating at least one selected from a minimum value, a maximum value, and an average value for at least one selected from i) a distance from the center line to the inner wall, ii) a distance from the center line to the outer wall, and iii) a thickness of a tissue.

According to one or more exemplary embodiments, an ultrasound diagnostic apparatus for an object having a tubular shape includes: an acquirer that acquires a center line which is formed in a long-axis direction of the object, and acquires distance data which includes at least one selected from a distance from the center line to an inner wall of the object and a distance from the center line to an outer wall of the object, based on ultrasound volume data of the object; a graph generator that generates an analysis graph, based on the center line and the distance data; and a display that displays the analysis graph.

The analysis graph may show a result which is obtained by calculating at least one selected from a minimum value, a maximum value, and an average value for at least one selected from i) a distance from the center line to the inner wall, ii) a distance from the center line to the outer wall, and iii) a thickness of a tissue.

According to one or more exemplary embodiments, an ultrasound diagnostic method for an object having a tubular shape includes: acquiring ultrasound volume data of the object; generating a virtual endoscope image which represents a surface of the object and at least one selected from blood flow, stiffness, a thickness of a wall, and contrast agent augmentation of an inside of the object, based on the ultrasound volume data; and displaying the virtual endoscope image.

According to one or more exemplary embodiments, an ultrasound diagnostic apparatus for an object having a tubular shape includes: an acquirer that acquires ultrasound volume data of the object; a virtual endoscope image generator that generates a virtual endoscope image which represents a surface of the object and at least one selected from blood flow, stiffness, a thickness of a wall, and contrast agent augmentation of an inside of the object, based on the ultrasound volume data; and a display that displays the virtual endoscope image.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
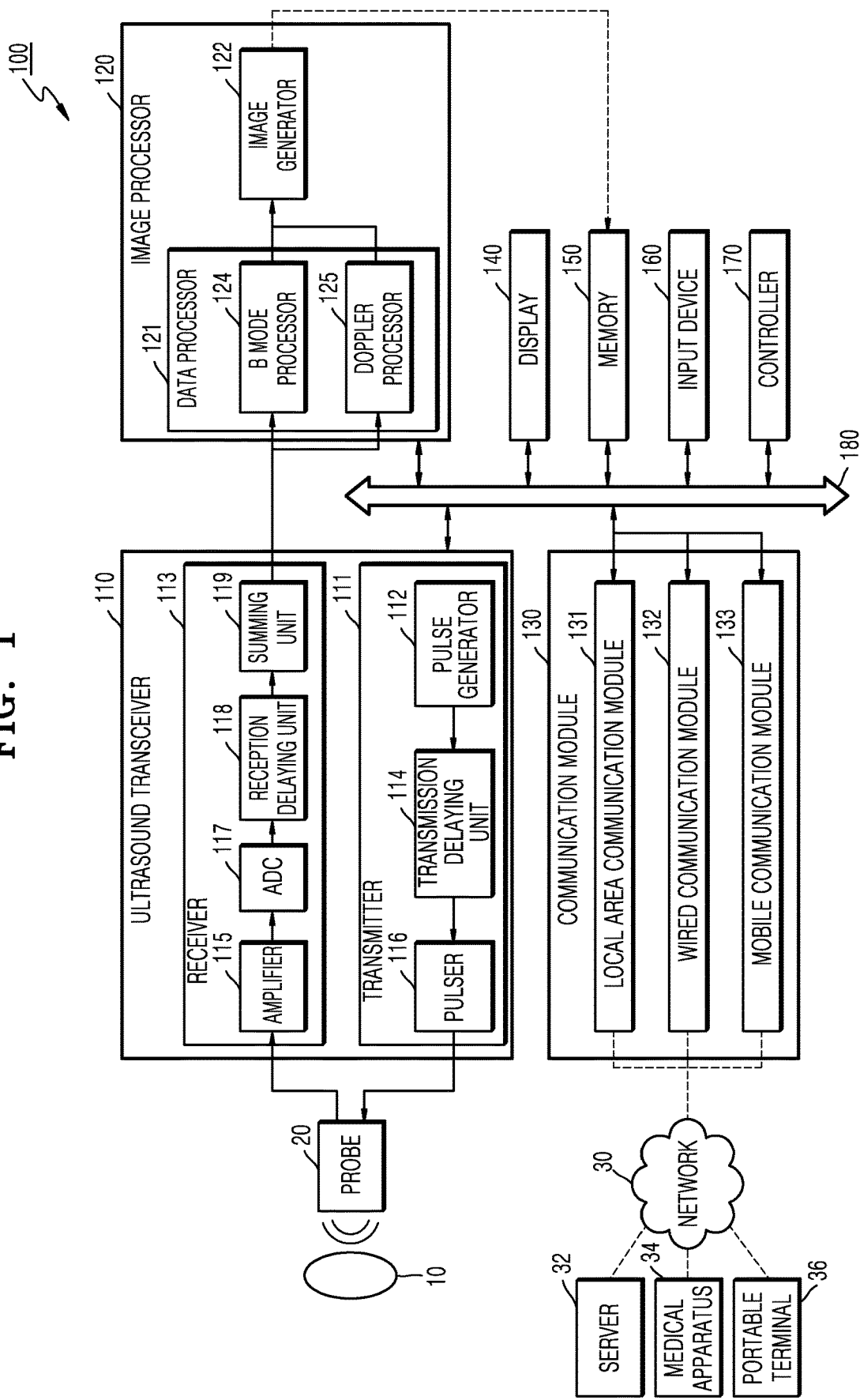
FIG. 1 is a block diagram illustrating a configuration of an ultrasound diagnostic apparatus according to an exemplary embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present description.

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used in the specification should be understood not as simple names but based on the meaning of the terms and the overall description of the invention.

Throughout the specification, it will also be understood that when a component "includes" an element, unless there is another opposite description thereto, it should be understood that the component does not exclude another element and may further include another element. In addition, terms such as " . . . unit", " . . . module", or the like refer to units that perform at least one function or operation, and the units may be implemented as hardware or software or as a combination of hardware and software.

Throughout the specification, an "ultrasound image" refers to an image of an object, which is obtained using ultrasound waves. Furthermore, an "object" may be a human, an animal, or a part of a human or animal. For example, the object may be an organ (e.g., the liver, the heart, the womb, the brain, a breast, or the abdomen), a blood vessel, or a combination thereof. Furthermore, the object may be a phantom. The phantom means a material having a density, an effective atomic number, and a volume that are approximately the same as those of an organism. For example, the phantom may be a spherical phantom having properties similar to a human body.

Throughout the specification, a "user" may be, but is not limited to, a medical expert, for example, a medical doctor, a nurse, a medical laboratory technologist, or a medical imaging expert, or a technician who repairs medical apparatuses.

Embodiments of the invention now will be described more fully hereinafter with reference to the accompanying drawings, in which illustrative embodiments of the invention are shown.

FIG. 1 is a block diagram showing a configuration of an ultrasound diagnosis apparatus 100 according to an embodiment. Referring to FIG. 1, the ultrasound diagnosis apparatus 100 may include a probe 20, an ultrasound transceiver 110, an image processor 120, a communication module 130, a display 140, a memory 150, an input device 160, and a controller 170, which may be connected to one another via buses 180.

The ultrasound diagnosis apparatus 100 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 110 and receives echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis apparatus 100 by wire or wirelessly.

A transmitter 111 supplies a driving signal to the probe 20. The transmitter 111 includes a pulse generator 112, a transmission delaying unit 114, and a pulser 116. The pulse generator 112 generates pulses for forming transmission ultrasound waves based on a predetermined pulse repetition frequency (PRF), and the transmission delaying unit 114 delays the pulses by delay times necessary for determining transmission directionality. The pulses which have been delayed correspond to a plurality of piezoelectric vibrators included in the probe 20, respectively. The pulser 116 applies a driving signal (or a driving pulse) to the probe 20 based on timing corresponding to each of the pulses which have been delayed.

A receiver 113 generates ultrasound data by processing echo signals received from the probe 20. The receiver 113 may include an amplifier 115, an analog-to-digital converter (ADC) 117, a reception delaying unit 118, and a summing unit 119. The amplifier 115 amplifies echo signals in each channel, and the ADC 117 performs analog-to-digital conversion with respect to the amplified echo signals. The reception delaying unit 118 delays digital echo signals output by the ADC 117 by delay times necessary for determining reception directionality, and the summing unit 119 generates ultrasound data by summing the echo signals processed by the reception delaying unit 118. In some embodiments, the receiver 113 may not include the amplifier 115. In other words, if the sensitivity of the probe 20 or the capability of the ADC 117 to process bits is enhanced, the amplifier 115 may be omitted.

The image processor 1200 generates an ultrasound image by scan-converting ultrasound data generated by the ultrasound transceiver 111 and displays the ultrasound image. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 124 extracts B mode components from ultrasound data and processes the B mode components. An image generator 122 may generate an ultrasound image indicating signal intensities as brightness based on the extracted B mode components.

Similarly, a Doppler processor 125 may extract Doppler components from ultrasound data, and the image generator 122 may generate a Doppler image indicating a movement of an object as colors or waveforms based on the extracted Doppler components.

According to an embodiment, the image generator 122 may generate a three-dimensional (3D) ultrasound image via volume-rendering with respect to volume data and may also generate an elasticity image by imaging deformation of the object 10 due to pressure. Furthermore, the image generator 122 may display various pieces of additional information in an ultrasound image by using text and graphics. In addition, the generated ultrasound image may be stored in the memory 150.

A display 140 displays the generated ultrasound image. The display 140 may display not only an ultrasound image, but also various pieces of information processed by the ultrasound diagnosis apparatus 100 on a screen image via a graphical user interface (GUI). In addition, the ultrasound diagnosis apparatus 100 may include two or more displays 140 according to embodiments.

The communication module 130 is connected to a network 30 by wire or wirelessly to communicate with an external device or a server. The communication module 130 may exchange data with a hospital server or another medical apparatus in a hospital, which is connected thereto via a PACS. Furthermore, the communication module 130 may perform data communication according to the digital imaging and communications in medicine (DICOM) standard.

The communication module 130 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 130 may receive information about a diagnosis history or medical treatment schedule of a patient from a server and utilizes the received information to diagnose the patient. Furthermore, the communication module 130 may perform data communication not only with a server or a medical apparatus in a hospital, but also with a portable terminal of a medical doctor or patient.

The communication module 130 is connected to the network 30 by wire or wirelessly to exchange data with a server 32, a medical apparatus 34, or a portable terminal 36. The communication module 130 may include one or more components for communication with external devices. For example, the communication module 130 may include a local area communication module 131, a wired communication module 132, and a mobile communication module 133.

The local area communication module 131 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 132 refers to a module for communication using electric signals or optical signals. Examples of wired communication techniques according to an embodiment may include communication via a twisted pair cable, a coaxial cable, an optical fiber cable, and an Ethernet cable.

The mobile communication module 133 transmits or receives wireless signals to or from at least one selected from a base station, an external terminal, and a server on a mobile communication network. The wireless signals may be voice call signals, video call signals, or various types of data for transmission and reception of text/multimedia messages.

The memory 150 stores various data processed by the ultrasound diagnosis apparatus 100. For example, the memory 150 may store medical data related to diagnosis of an object, such as ultrasound data and an ultrasound image that are input or output, and may also store algorithms or programs which are to be executed in the ultrasound diagnosis apparatus 100.

The memory 150 may be any of various storage media, e.g., a flash memory, a hard disk drive, EEPROM, etc. Furthermore, the ultrasound diagnosis apparatus 100 may utilize web storage or a cloud server that performs the storage function of the memory 150 online.

The input device 160 refers to a means via which a user inputs data for controlling the ultrasound diagnosis apparatus 100. The input device 160 may include hardware components, such as a keypad, a mouse, a touch pad, a touch screen, and a jog switch. However, embodiments are not limited thereto, and the input device 160 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The controller 170 may control all operations of the ultrasound diagnosis apparatus 100. In other words, the controller 170 may control operations among the probe 20, the ultrasound transceiver 110, the image processor 120, the communication module 130, the display 140, the memory 150, and the input device 160 shown in FIG. 1.

All or some of the probe 20, the ultrasound transceiver 110, the image processor 120, the communication module 130, the display 140, the memory 150, the input device 160, and the controller 170 may be implemented as software modules. However, embodiments are not limited thereto, and some of the components stated above may be implemented as hardware modules. Furthermore, at least one selected from the ultrasound transceiver 110, the image processor 120, and the communication module 130 may be included in the controller 170. However, embodiments are not limited thereto.

Figure 2:
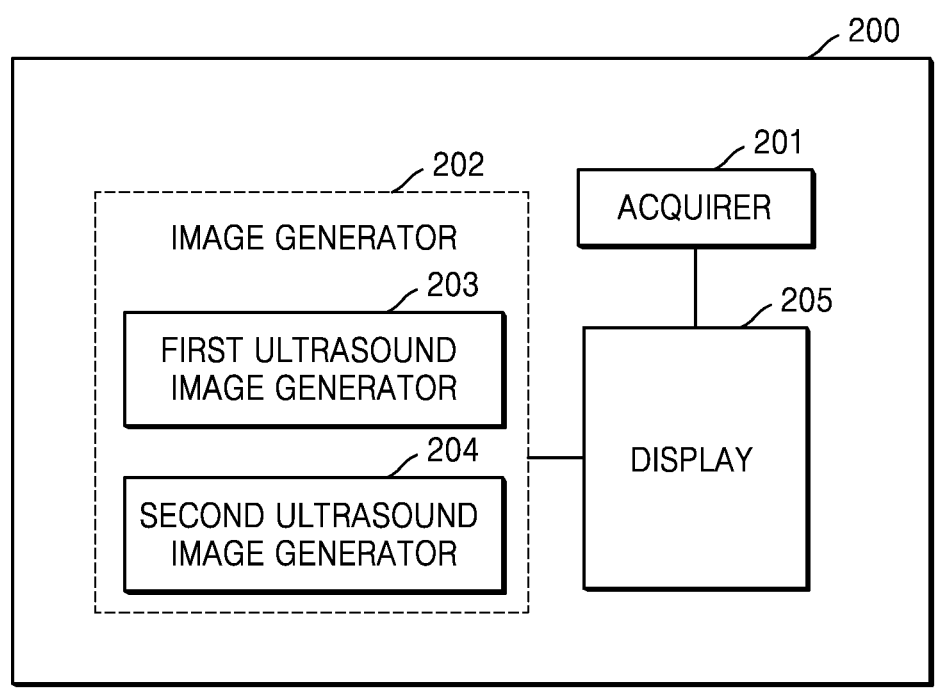
FIG. 2 is a block diagram illustrating a configuration of an ultrasound diagnostic apparatus according to an exemplary embodiment.

FIG. 2 is a block diagram illustrating a configuration of an ultrasound diagnostic apparatus 200 according to an exemplary embodiment.

As illustrated in FIG. 2, the ultrasound diagnostic apparatus 200 according to an exemplary embodiment may include an acquirer 201, an image generator 202 including a first ultrasound image generator 203 and a second ultrasound image generator 204, and a display 205.

The ultrasound diagnostic apparatus 200 according to an exemplary embodiment may be an apparatus for diagnosing a tubular object by using an ultrasound wave. The acquirer 201 may acquire ultrasound volume data of an object, and the first ultrasound image generator 203 may generate a first ultrasound image which is obtained by imaging a surface of the object, based on the ultrasound volume data. The first ultrasound image obtained by imaging the surface of the object may include, for example, an image representing a surface of a tubular object. The image representing the surface of the object is not limited to an image representing a surface itself of a wall of an object, and for example, may include at least one selected from an image representing a position of an inner wall of an object, an image representing a position of an outer wall of the object, and an image representing a position which connects centers of the inner wall and outer wall of the object. The second ultrasound image generator 204 may generate a second ultrasound image which is obtained by imaging information about the inside of the object included in the first ultrasound image, based on the ultrasound volume data. The display 205 may display the first ultrasound image and the second ultrasound image. The information about the inside of the object may include information about at least one selected from an internal blood flow of the object, stiffness, a thickness of a wall, and contrast agent augmentation.

Moreover, according to another exemplary embodiment, the acquirer 201 of the ultrasound diagnostic apparatus 200 may acquire ultrasound volume data of an object, and the first ultrasound image generator 203 may generate a first ultrasound image representing a surface of the object, based on the ultrasound volume data. The second ultrasound image generator 204 may generate a second ultrasound image representing at least one selected from a plane corresponding to a surface of an inner wall and a plane corresponding to a surface of an outer wall, based on the ultrasound volume data. The display 205 may display the first ultrasound image and the second ultrasound image.

Here, the tubular object includes body tissue representing a tubular shape, which includes an inner wall and an outer wall. Examples of the tubular object may include digestive organs such as a small intestine, a large intestine, a stomach, an esophagus, a duodenum, and a liver. Also, examples of the tubular object may further include a blood vessel, a biliary tract, a bile duct, a gall bladder, a ductus cysticus, a lymphatic vessel, a mammary gland, and a ductus lactiferi, but the tubular object is not limited thereto.

Moreover, the first ultrasound image representing the surface of the object includes an image in which the surface of the object is shown, and a form of displaying a surface is not limited. The first ultrasound image representing the surface of the object may include a virtual endoscope image and a slice image.

Here, the virtual endoscope image is an image having the same view as that of an image which is obtained through an endoscope, and may be an image which is generated based on ultrasound volume data. The virtual endoscope image may be displayed by using a method such as fish's eye and perspective. In the present specification, for convenience of a description, a case in which the virtual endoscope image is displayed by using the perspective will be described (see FIGS. 4 to 7).

A view may denote a method in which an ultrasound image diagnostic apparatus displays an image of an object on a screen so as to diagnose an anatomical abnormality of the object or analyze a motion.

A user more intuitively recognizes an inner surface of a tubular object by using a virtual endoscope image.

According to an exemplary embodiment, an image representing a surface of a tubular object may be represented as a navigation view.

Here, the navigation view denotes a display method that represents a center line of the inside of an object. A cursor may be positioned on a center line, which is marked on the navigation view. The cursor may be moved along the center line, based on a user input, and a user may move the cursor to an ROI to select the ROI. Hereinafter, an image having the navigation view is referred to as a navigation image.

Hereinafter, exemplary embodiments in which a slice of an object is marked on a navigation image will be described in detail. However, an arbitrary image, which enables a center line of the inside to be marked, may be represented as a navigation image, and thus, the navigation image is not limited to an image in which a slice is marked. This will be described in detail with reference to FIGS. 7 to 12.

Referring to FIG. 2, the acquirer 201 may acquire ultrasound data about an object. The ultrasound data according to an exemplary embodiment includes ultrasound volume data.

According to an exemplary embodiment, the acquirer 201 may include a probe (not shown) and an ultrasound transceiver (not shown) for transmitting or receiving an ultrasound signal. The probe and the ultrasound transceiver included in the acquirer 201 may respectively correspond to the probe 20 and ultrasound transceiver 110 of FIG. 1.

The image generator 202 may include the first ultrasound image generator 203 and the second ultrasound image generator 204. Also, the image generator 202 may be included in the image processor 120 of FIG. 1. In this case, the image generator 202 may correspond to the image generator 122 of FIG. 1.

The first ultrasound image generator 203 may generate an image which is obtained by imaging a surface of the object, based on the ultrasound volume data acquired by the acquirer 201.

According to an exemplary embodiment, for example, the first ultrasound image generator 203 may generate a virtual endoscope image of the object. Also, the first ultrasound image generator 203 may generate an image representing a slice that is parallel to an axial direction of the object or an image representing a slice that is vertical to the axial direction, based on the ultrasound volume data.

Here, the axial direction of the object denotes a length direction of a tubular object.

According to an exemplary embodiment, the second ultrasound image generator 204 may generate a second ultrasound image representing information about the inside of the object included in the first ultrasound image, based on the ultrasound volume data.

Here, the inside of the object includes an inner wall of the object, an outer wall of the object, tissue that is surrounded by the inner wall and outer wall of the object, a blood vessel included in the object, and lesion tissue generated in the object. To diagnose an object having Crohn's disease, since a wall of a colon swells or a perforation is formed, the inside of the object may be observed. Also, to diagnose a tubular object, both information of a surface of the tubular object and information about the inside of the tubular object may be used.

The information about the inside of the object may include at least one selected from information about an internal blood flow of the object, information about elasticity of the object, information about the contrast agent augmentation of the object, and a thickness of the object.

The second ultrasound image generator 204 may generate at least one selected from a color Doppler image, an elasticity image, and a contrast agent augmentation image, which represent information about the inside of the object. In detail, the second ultrasound image generator 204 may generate the color Doppler image representing information about the internal blood flow of the object. The second ultrasound image generator 204 may generate the elasticity image, based on information about elasticity of the object. The second ultrasound image generator 204 may generate the contrast agent augmentation image, based on information about a contrast agent augmentation characteristic of the object. Also, the second ultrasound image generator 204 may generate an image representing a thickness of a wall of the object. In an exemplary embodiment, a thickness of a wall may be displayed by applying a color, corresponding to a thickness of the object, to an image of the object.

The color Doppler image is referred to as a blood flow Doppler image representing blood flow, and may represent a speed of blood flow. The elasticity image is an image which is obtained by imaging a deformation degree of the object caused by pressure, and may represent elasticity of the object. The contrast agent augmentation image may represent a reactivity difference between contrast agents of respective parts of the object when a contrast agent is injected into the object. The contrast agent denotes a drug which is injected into a stomach, an intestinal canal, a blood vessel, a cerebrospinal canal, and a joint cavity and enables a user to look at tissue or a blood vessel in a diagnosis using ultrasound photographing. Also, the second ultrasound image generator 204 may acquire distance data which includes at least one selected from a distance from a center line to an inner wall and a distance from the center line to an outer wall, and generate an analysis graph, based on the center line and the distance data.

Here, the center line may be a line which connects center positions of the inside of a tubular object. An inner wall of an object may be extracted from a slice parallel to or vertical to an axis of the tubular object. The center line may be acquired by connecting points which correspond to center positions with respect to the extracted inner wall.

The second ultrasound image generated by the second ultrasound image generator 204 is not limited to the above description, and may include all images capable of representing information about the inside of an object.

The second ultrasound image generator 204 may generate the second ultrasound image corresponding to an ROI selected from the first ultrasound image, based on a user input.

For example, the ultrasound diagnostic apparatus 200 may receive a user input which selects at least one from a point, a line, and a region of the first ultrasound image, and set an ROI. In this case, the user input may be an input which is received by using an input device such as a mouse or a keypad, and when the display 205 is configured with a touch screen, the user input may be a touch input which is received by using a touch tool (for example, a finger, an electronic pen, or the like). A cursor may be displayed on the display 205, for the user input.

The display 205 may display the first ultrasound image and the second ultrasound image.

Moreover, the display 205 may display information processed by the ultrasound diagnostic apparatus 200.

For example, the display 205 may display an ultrasound image of an object on a screen, or display a user interface (UI) or a graphical user interface (GUI) associated with a function setting.

When a touch pad (for example, a contact capacitive type, a press resistive type, an infrared sensing type, a surface ultrasound conductive type, an integration tension measurement type, and a piezo effect type) forms a layer structure along with a display panel to configure a touch screen, the display 205 may be used as an input device in addition to an output device. The display 205 may include at least one selected from a liquid crystal display (LCD), a thin film transistor-liquid crystal display, an organic light-emitting diode (OLED) display, a flexible display, a 3D display, and an electrophoretic display.

The display 205 may display the second ultrasound image to overlap the first ultrasound image.

According to an exemplary embodiment, the display 205 may display the first ultrasound image and the second ultrasound image to overlap each other through weighted sum. This will be described below in detail with reference to FIG. 5.

The display 205 may display the first ultrasound image on which a center line formed in the axial direction of the object is marked.

The display 205 may display the first ultrasound image on a first region of a screen, and display the second ultrasound image, corresponding to an ROI selected from the first ultrasound image, on a second region of the screen.

The second ultrasound image corresponding to the ROI selected from the first ultrasound image includes a virtual endoscope image generated by the second ultrasound image generator 204 and a color Doppler image, an elasticity image, a contrast agent augmentation image, and an analysis graph of the inside of the object generated by the second ultrasound image generator 204.

However, the second ultrasound image corresponding to the selected ROI is not limited to the examples, and may be an ultrasound image representing at least one selected from a plane corresponding to a surface of an inner wall and a plane corresponding to a surface of an outer wall.

The display 205 may mark a cursor, which is used to set an ROI on the center line which is formed in the axial direction of the object, on the first ultrasound image. The cursor may be moved along the center line, based on a user input.

The display 205 of FIG. 2 may correspond to the display 140 of FIG. 1.

The ultrasound diagnostic apparatus 200 of FIG. 2 may further include a controller (not shown). The controller may control an operation of the ultrasound diagnostic apparatus 200. Also, the controller may control operations of the acquirer 201, the image generator 202, and the display 205. The controller may correspond to the controller 160 of FIG. 1.

Figure 3A:
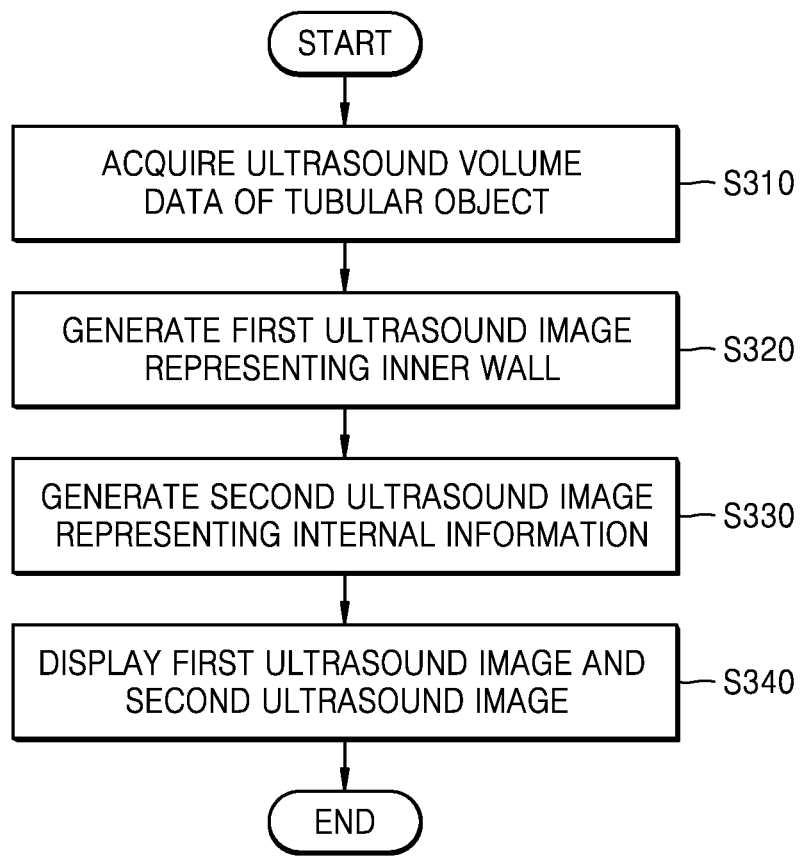
FIG. 3A is a flowchart for describing an ultrasound diagnostic method according to an exemplary embodiment.

FIG. 3A is a flowchart for describing an ultrasound diagnostic method according to an exemplary embodiment.

In operation S310, the acquirer 201 may acquire ultrasound volume data of an object.

In operation S320, the first ultrasound image generator 203 may generate a first ultrasound image which is obtained by imaging a surface of the object, based on the ultrasound volume data.

In operation S330, the second ultrasound image generator 204 may generate a second ultrasound image which is obtained by imaging information about the inside of the object included in the first ultrasound image, based on the ultrasound volume data.

The second ultrasound image may include a color Doppler image, an elasticity image, and a contrast agent augmentation image of the inside of the object included in the first ultrasound image. Also, the second ultrasound image may include a virtual endoscope image and an analysis graph.

In operation S340, the display 205 may display the first ultrasound image and the second ultrasound image.

Figure 3B:
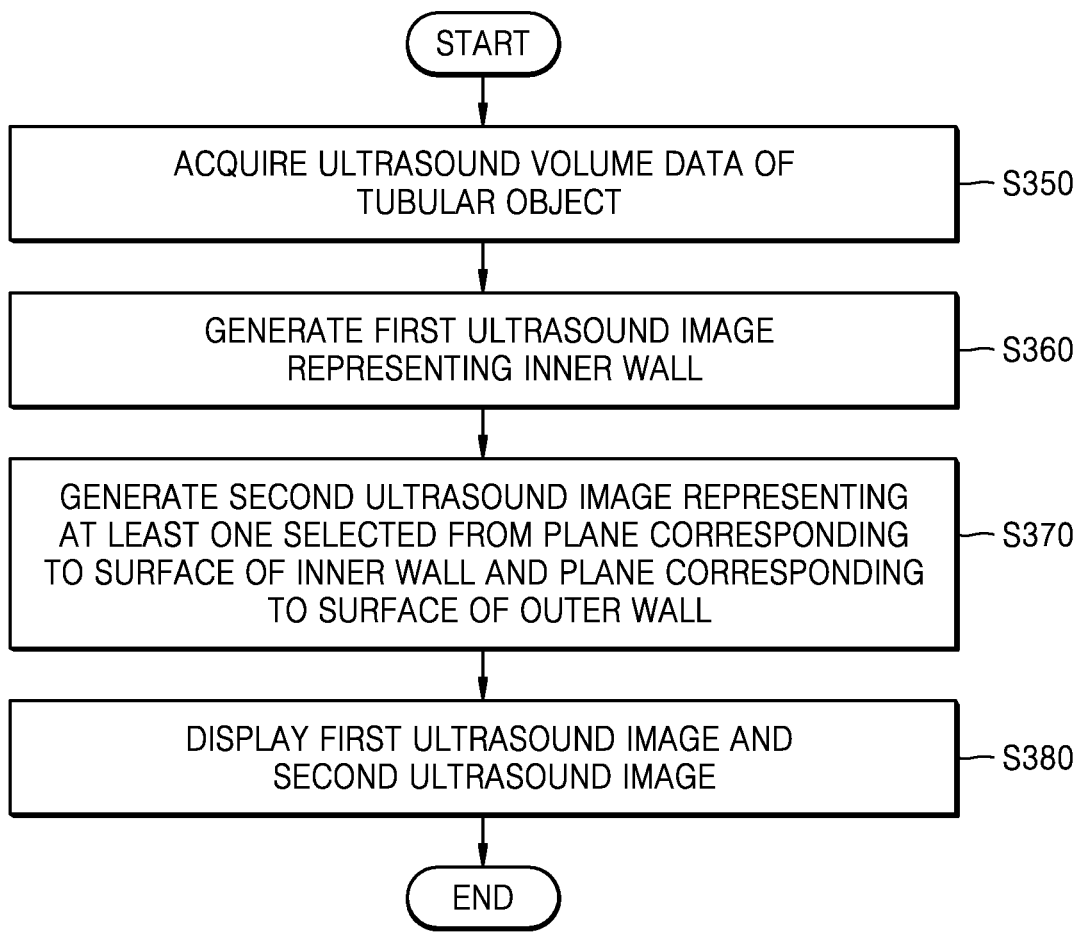
FIG. 3B is a flowchart for describing an ultrasound diagnostic method according to an exemplary embodiment.

FIG. 3B is a flowchart for describing an ultrasound diagnostic method according to an exemplary embodiment.

In operation S350, the acquirer 201 may acquire ultrasound volume data of an object.

In operation S360, the first ultrasound image generator 203 may generate a first ultrasound image representing a surface of the object, based on the ultrasound volume data.

In operation S370, the second ultrasound image generator 204 may generate a second ultrasound image which represents at least one selected from a plane corresponding to a surface of an inner wall and a plane corresponding to a surface of an outer wall, based on the ultrasound volume data.

In operation S380, the display 205 may display the first ultrasound image and the second ultrasound image.

Figure 4:
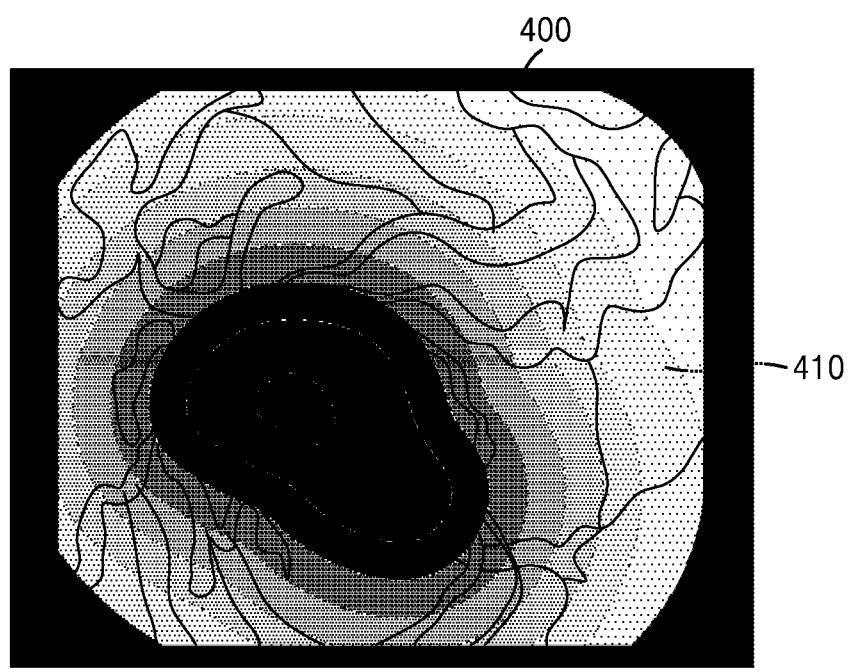
FIG. 4 is a diagram illustrating an example of a first ultrasound image according to an exemplary embodiment.

FIG. 4 is a diagram illustrating an example of a first ultrasound image 400 according to an exemplary embodiment.

The first ultrasound image 400 is an ultrasound image which is generated by imaging a surface, based on ultrasound volume data. In FIG. 4, a case where the first ultrasound image 400 according to an exemplary embodiment is a virtual endoscope image representing an inner wall 410 of an object is illustrated. However, the first ultrasound image 400 is not limited to the exemplary embodiment, and may be a navigation image representing the inner wall 410. Also, the first ultrasound image 400, which is obtained by imaging a surface of the object, may include a slice image. The slice image may represent an arbitrary slice of the object.

The first ultrasound image 400 of FIG. 4 shows the inside of a tubular object as seen in an axial direction of the object by using a virtual endoscope. A portion of the inner wall 410 of FIG. 4, which is shown in a deep color, may be a portion far away from a viewing position. That is, an inner wall of an object may be three-dimensionally shown like a screen seen through an endoscope.

In FIG. 4, a case where an object is a digestive organ such as an esophagus, a stomach, a large intestine, or a small intestine is illustrated, but the present embodiment is not limited thereto.

Hereinafter, examples of a screen displayed by the display 205 will be described in detail with reference to FIGS. 5 to 12.

Figure 5:
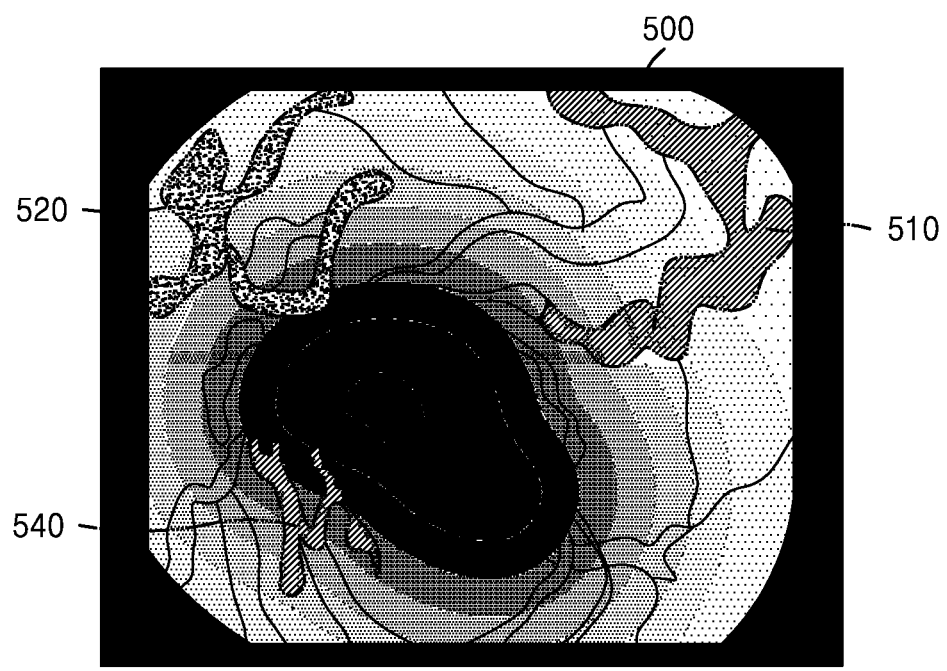
FIG. 5 is a diagram illustrating an example of a screen displaying a first ultrasound image and a second ultrasound image, according to an exemplary embodiment.
Figure 5:
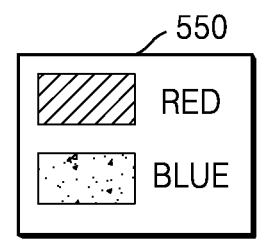

FIG. 5 is a diagram illustrating an example of a screen displaying a first ultrasound image and a second ultrasound image, according to an exemplary embodiment.

Referring to FIG. 5, the first ultrasound image and the second ultrasound image may be displayed as one image 500 by overlapping each other.

FIG. 5 illustrates a case where the first ultrasound image is a virtual endoscope image representing an inner wall of an object. In detail, a case where an object is a digestive organ such as an esophagus, a stomach, a large intestine, or a small intestine is illustrated in FIG. 5, but the present embodiment is not limited thereto.

As illustrated in FIG. 5, the second ultrasound image may include a blood flow Doppler image, which represents blood flow of the inside of an object included in the first ultrasound image. The second ultrasound image may be displayed to overlap the first ultrasound image through a weight sum. For example, when a weight value of the second ultrasound image is 0.3 and a weight value of the first ultrasound image is 0.7, the first and second ultrasound images may be displayed as one image by summating the first and second ultrasound images. In the image 500, a portion, which is faster than a certain speed, is shown in red 510 and 540, and a portion, which is slower than the certain speed, is shown in blue 520, for representing different speeds of blood flow.

As illustrated in FIG. 5, a color 550 representing blood flow which is marked on the image 500 is not limited to red or blue, and another color may be additionally used for representing blood flows of various ranges.

Figure 6:
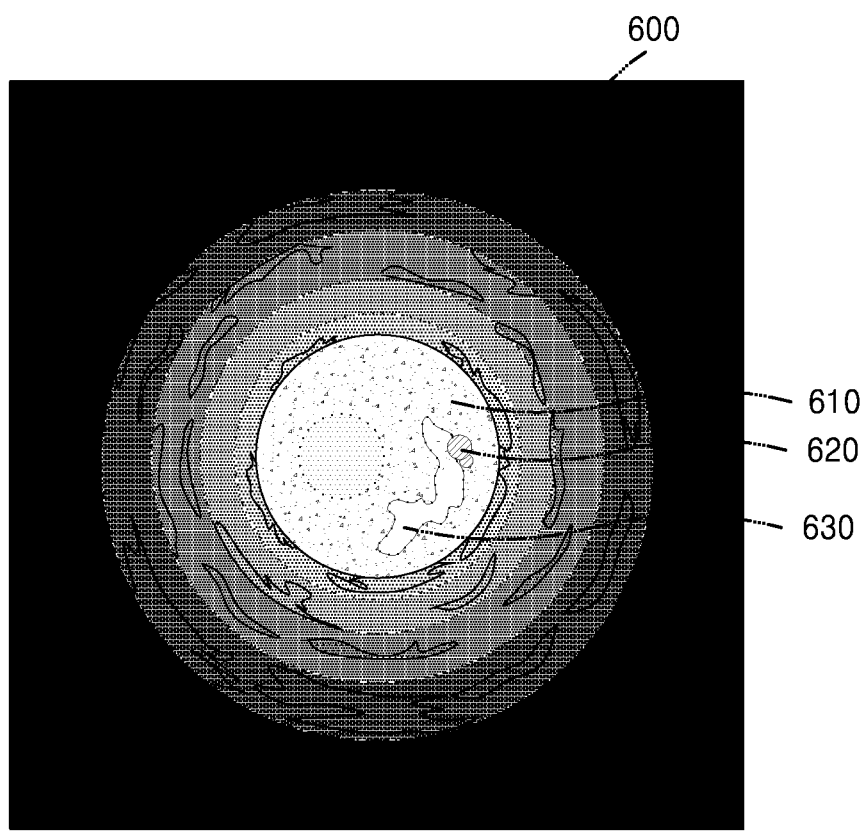
FIG. 6 is a diagram illustrating another example of a screen displaying a first ultrasound image and a second ultrasound image, according to an exemplary embodiment.
Figure 6:
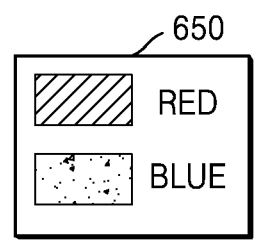

FIG. 6 is a diagram illustrating another example of a screen displaying a first ultrasound image and a second ultrasound image, according to an exemplary embodiment.

Similarly to the description of FIG. 5, the first ultrasound image and the second ultrasound image may be displayed as one image 600 by overlapping each other.

FIG. 6 illustrates a case where the first ultrasound image is a virtual endoscope image representing an inner wall of an object. FIG. 6 illustrates the inside of a tubular object as seen in an axial direction of the object by using a virtual endoscope. In FIG. 6, a portion in which a surface of an inner wall is illustrated in a deep color may be a portion close to a viewing position. In detail, the object of FIG. 6 may be a digestive organ, such as an esophagus, a stomach, a large intestine, or a small intestine, a blood vessel, or a lymphatic vessel, but the present embodiment is not limited thereto.

The second ultrasound image of FIG. 6 may be an image which represents elasticity, a contrast agent augmentation characteristic, and a thickness of the inside of the object included in the first ultrasound image. Similarly to the description of FIG. 5, the second ultrasound image may be displayed to overlap the first ultrasound image through a weight sum.

In the image 600, in order to represent different elasticity, a portion 620 having elasticity within a first elasticity range may be shown in red, a portion 610 having elasticity within a second elasticity range may be shown in blue, and a portion 630 having elasticity within a third elasticity range may be shown in white. Also, a color 650 representing elasticity is not limited to red or blue of FIG. 6, and various colors may be used.

Figure 7:
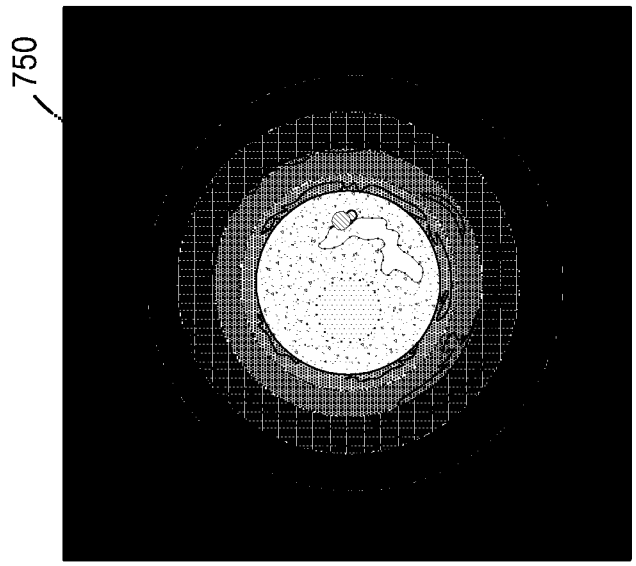
FIG. 7 is a diagram illustrating another example of a screen displaying a first ultrasound image and a second ultrasound image, according to an exemplary embodiment.
Figure 7:
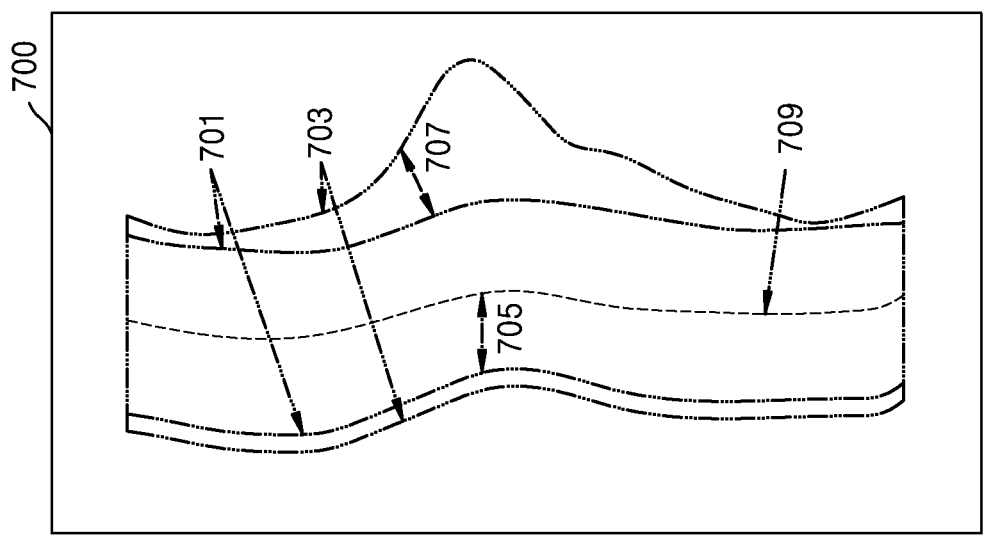

FIG. 7 is a diagram illustrating another example of a screen displaying a first ultrasound image and a second ultrasound image, according to an exemplary embodiment.

As illustrated in FIG. 7, a first ultrasound image 700 and a second ultrasound image 750 may be displayed in different regions. Here, a region in which the first ultrasound image 700 is displayed is referred to as a first region, and a region in which the second ultrasound image 750 is displayed is referred to as a second region.

According to an exemplary embodiment, the first ultrasound image 700 may be displayed as a navigation view representing a center line 709 of the inside of an object. The second ultrasound image 750 may be a virtual endoscope image.

The first ultrasound image 700 of FIG. 7 represents the center line 709 of the object, which is marked on an image representing a slice parallel to an axial direction of the object. As described above, in FIGS. 7 to 12, a navigation image is illustrated as representing a slice of the object. However, an arbitrary image capable of displaying the center line 709 may be represented as the navigation image, and thus, the navigation image is not limited to the form illustrated in FIG. 7.

An inner wall 701 and an outer wall 703 of the object may be marked on the first ultrasound image 700. Also, the center line 709, a distance 705 from the center line 709 to the inner wall 701, and a thickness 707 of the object may be further marked on the first ultrasound image 700.

The second ultrasound image 750 may represent information about the inside of the object included in the first ultrasound image 700. The second ultrasound image 750 may include the image 600 described above with reference to FIG. 6.

That is, the second ultrasound image 750 may be a virtual endoscope image in which the information about the inside of the object is marked. This has been described above with reference to FIG. 6, and thus, a detailed description is not provided.

Figure 8:
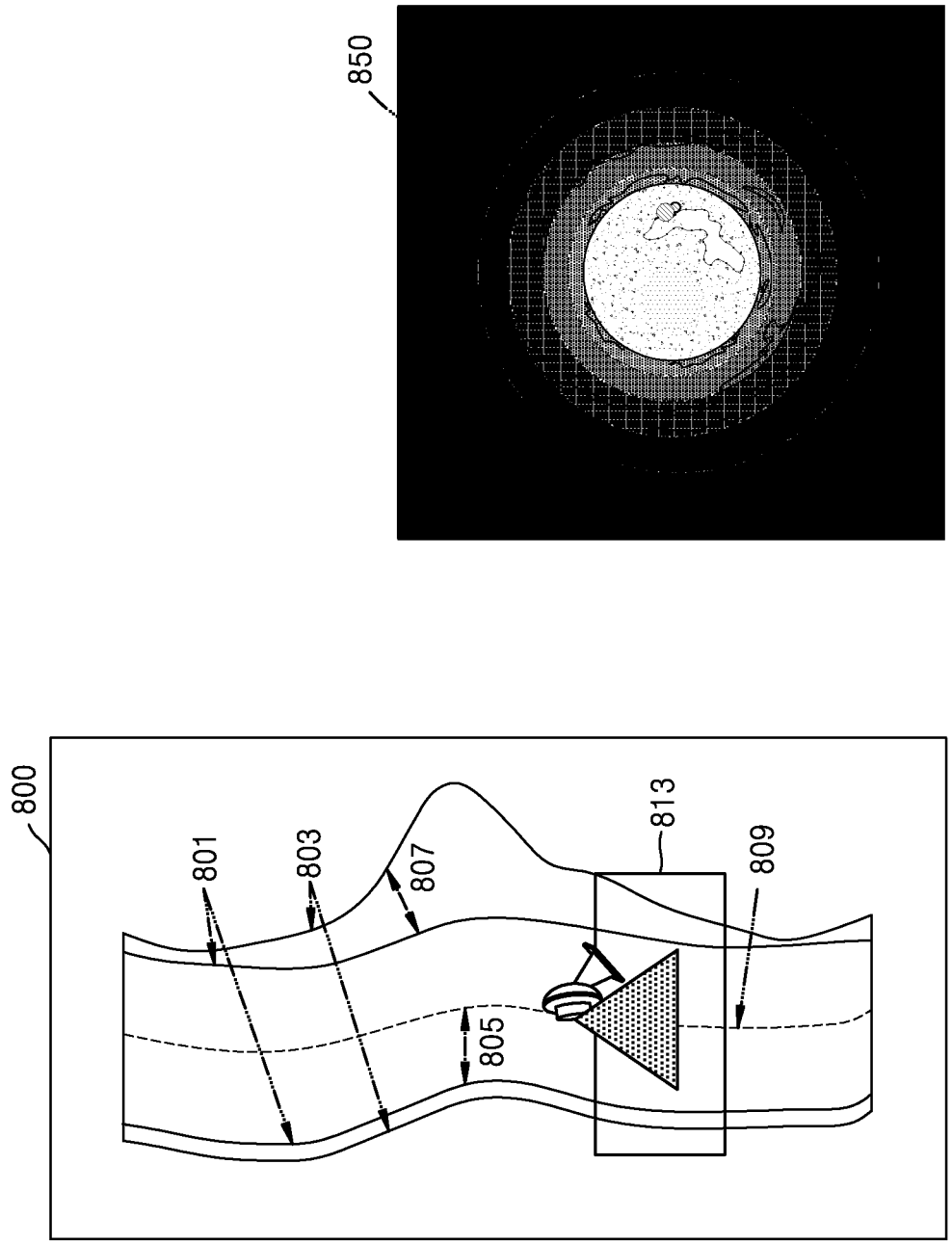
FIG. 8 is a diagram illustrating an example of a screen displaying a first ultrasound image and a second ultrasound image corresponding to an ROI, according to an exemplary embodiment.

FIG. 8 is a diagram illustrating an example of a screen displaying a first ultrasound image and a second ultrasound image corresponding to an ROI, according to an exemplary embodiment.

Except that a cursor 811 is positioned on a center line 809, a first ultrasound image 800 of FIG. 8 is the same as the first ultrasound image 700 of FIG. 7, and thus, the same descriptions provided with regard to FIG. 7 are not repeated. The cursor 811 may be moved along the center line 809, based on a user input, and a user may move the cursor 811 to an ROI 813 to select the ROI 813.

A second ultrasound image 850 may be an image corresponding to the ROI 813, which is selected by the cursor 811 from an object included in the first ultrasound image 800.

The cursor 811 is illustrated as being moved along the center line 809, but is not limited thereto. The cursor 811 may be moved to a portion which is set by the user. A form in which the cursor 811 is displayed is not limited to the form illustrated in FIG. 8, and the cursor 811 may be displayed in various forms.

A figure representing an ROI may be displayed on the ROI 813 so as to know which portion of the first ultrasound image 800 the second ultrasound image 850 corresponds to. The figure may be displayed in a tetragonal shape or as a line or a dot line. However, the figure representing the ROI may not be marked on the first ultrasound image 800.

According to an exemplary embodiment, the user may select the ROI 813 of the object included in the first ultrasound image 800 through only simple manipulation, and thus, easily determines elasticity, a contrast agent characteristic, and a thickness of the inside of the selected ROI 813 by using the second ultrasound image 850.

Figure 9:
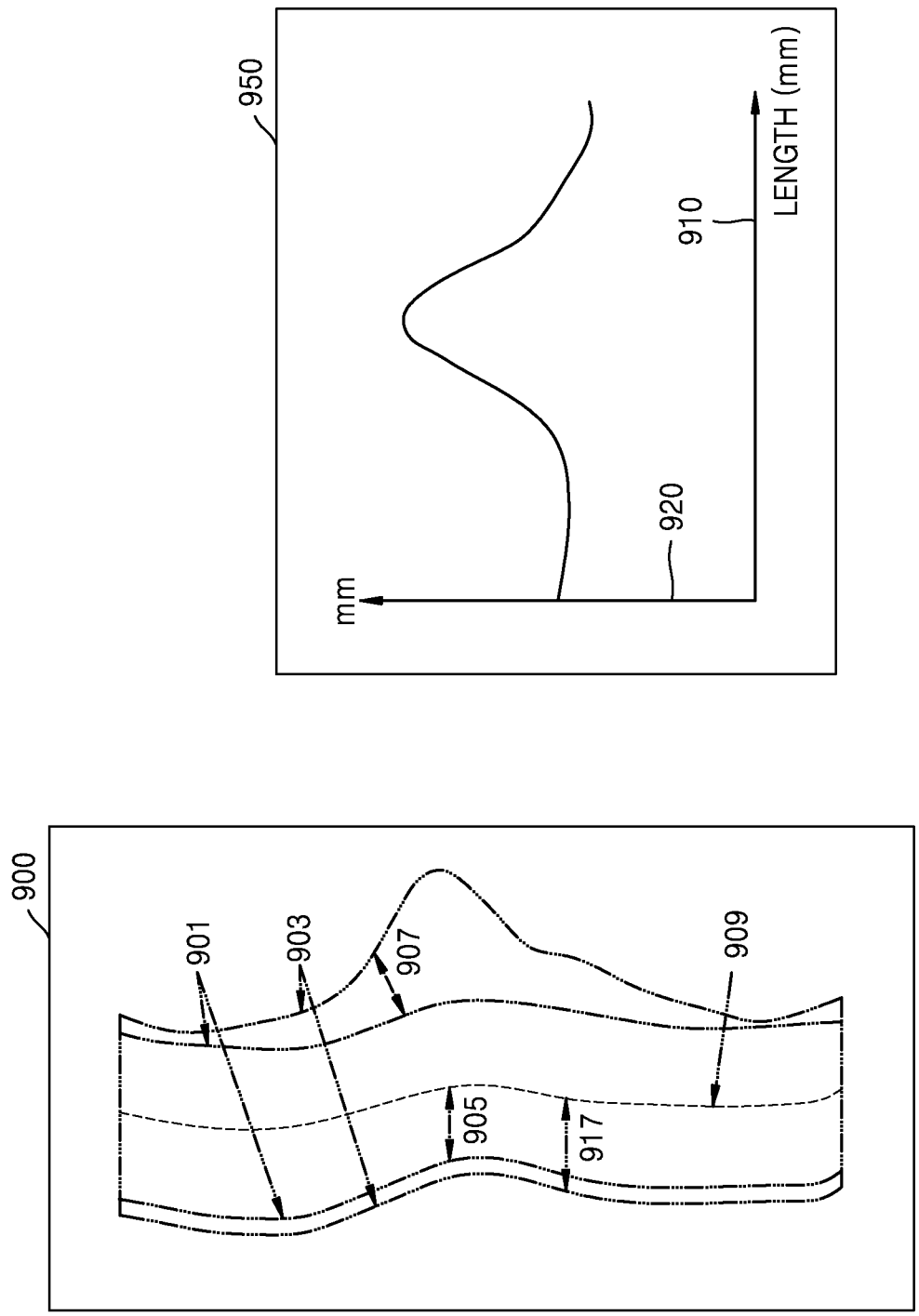
FIG. 9 is a diagram illustrating another example of a screen displaying a first ultrasound image and a second ultrasound image corresponding to an ROI, according to an exemplary embodiment.

FIG. 9 is a diagram illustrating another example of a screen displaying a first ultrasound image and a second ultrasound image corresponding to an ROI, according to an exemplary embodiment.

An inner wall 901 and an outer wall 903 of an object may be marked on a first ultrasound image 900. Also, a center line 909, a distance 905 from the center line 909 to the inner wall 901, a distance 917 from the center line 909 to the outer wall 903, and a thickness 907 of the object may be further marked on the first ultrasound image 900.

The first ultrasound image 900 of FIG. 9 may correspond to the first ultrasound image 700 of FIG. 7. This has been described in detail with reference to FIG. 7, and thus, a detailed description is not provided.

A second ultrasound image 950 may represent information about the inside of the object included in the first ultrasound image 900.

The second ultrasound image 950 may represent an analysis graph, based on the center line 909 and distance data which includes at least one selected from the distance 905 from the center line 909 to the inner wall 901 and the distance 917 from the center line 909 to the outer wall 903, which are marked on the first ultrasound image 900.

An abscissa axis 910 of the analysis graph may indicate a position on the center line 909. For example, a range of the abscissa axis 910 may match a range of the center line 909 which is marked on the first ultrasound image 900. That is, a lower end of the center line 909 may correspond to a leftmost side of the abscissa axis 910, and an upper end of the center line 909 may correspond to a rightmost side of the abscissa axis 910. The range of the abscissa axis 910 may be changed according to a user input. An ordinate axis 920 of the analysis graph may indicate at least one selected from the distance 905 from the center line 909 to the inner wall 901, the distance 917 from the center line 909 to the outer wall 903, and the thickness 907 of the object. A kind of data shown on the ordinate axis 920 may be changed according to a user input.

The analysis graph may show a result which is obtained by calculating at least one selected from a minimum value, a maximum value, and an average value for at least one selected from i) the distance 905 from the center line 909 to the inner wall 901, ii) the distance 917 from the center line 909 to the outer wall 903, and iii) the thickness 907 of the object.

Figure 10:
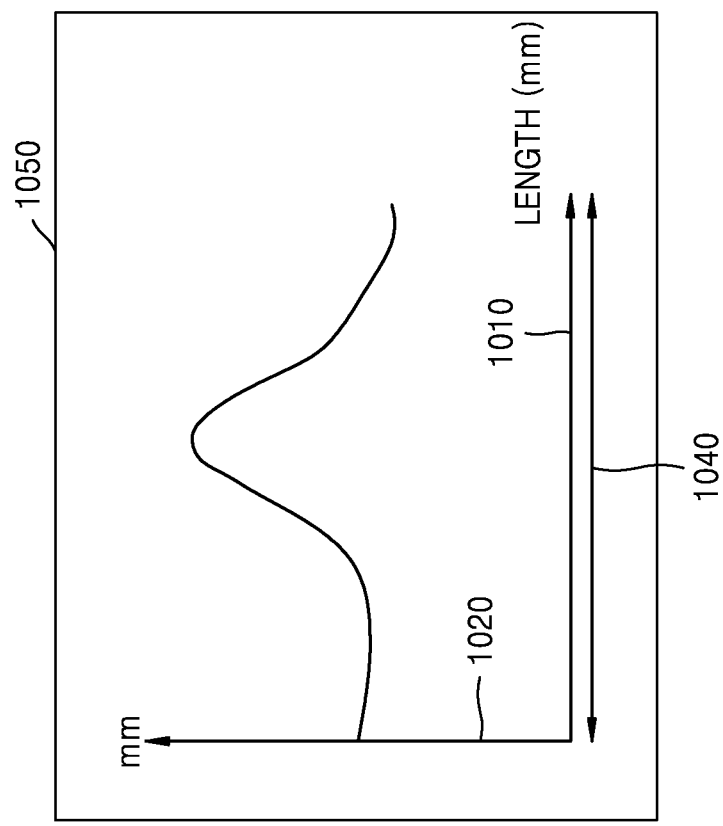
FIG. 10 is a diagram illustrating another example of a screen displaying a first ultrasound image and a second ultrasound image corresponding to an ROI, according to an exemplary embodiment.
Figure 10:
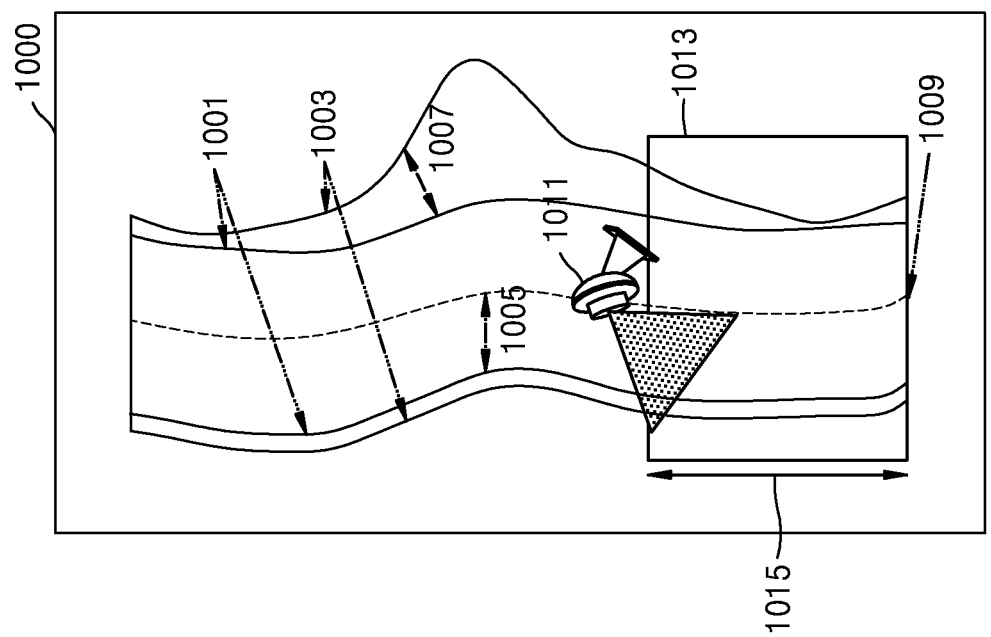

FIG. 10 is a diagram illustrating another example of a screen displaying a first ultrasound image and a second ultrasound image corresponding to an ROI, according to an exemplary embodiment.

Except that a cursor 1011 is positioned on a center line 1009, a first ultrasound image 1000 of FIG. 10 is the same as the first ultrasound image 900 of FIG. 9, and thus, the same descriptions provided with regard to FIG. 9 are not repeated. The cursor 1011 may be moved along the center line 1009, based on a user input, and a user may move the cursor 1011 to an ROI 1013 to select the ROI 1013.

A second ultrasound image 1050 is an analysis graph corresponding to the ROI 1013 which is selected by the cursor 1011 from an object included in the first ultrasound image 1000.

The user may designate a range 1040 of an abscissa axis 1010 of the analysis graph by using the cursor 1011. The abscissa axis 1010 may indicate a position on the center line 1009. Therefore, the range 1040 of the abscissa axis 1010 may correspond to a range 1015 which is marked in a center-line direction of the ROI 1013.

According to the present embodiment, the second ultrasound image 1050 corresponding to an ROI may be displayed even without user's obtaining ultrasound volume data again for looking at another view. That is, a diagnosis is easily performed by using an analysis graph of a region selected from the first ultrasound image 1000.

Figure 11:
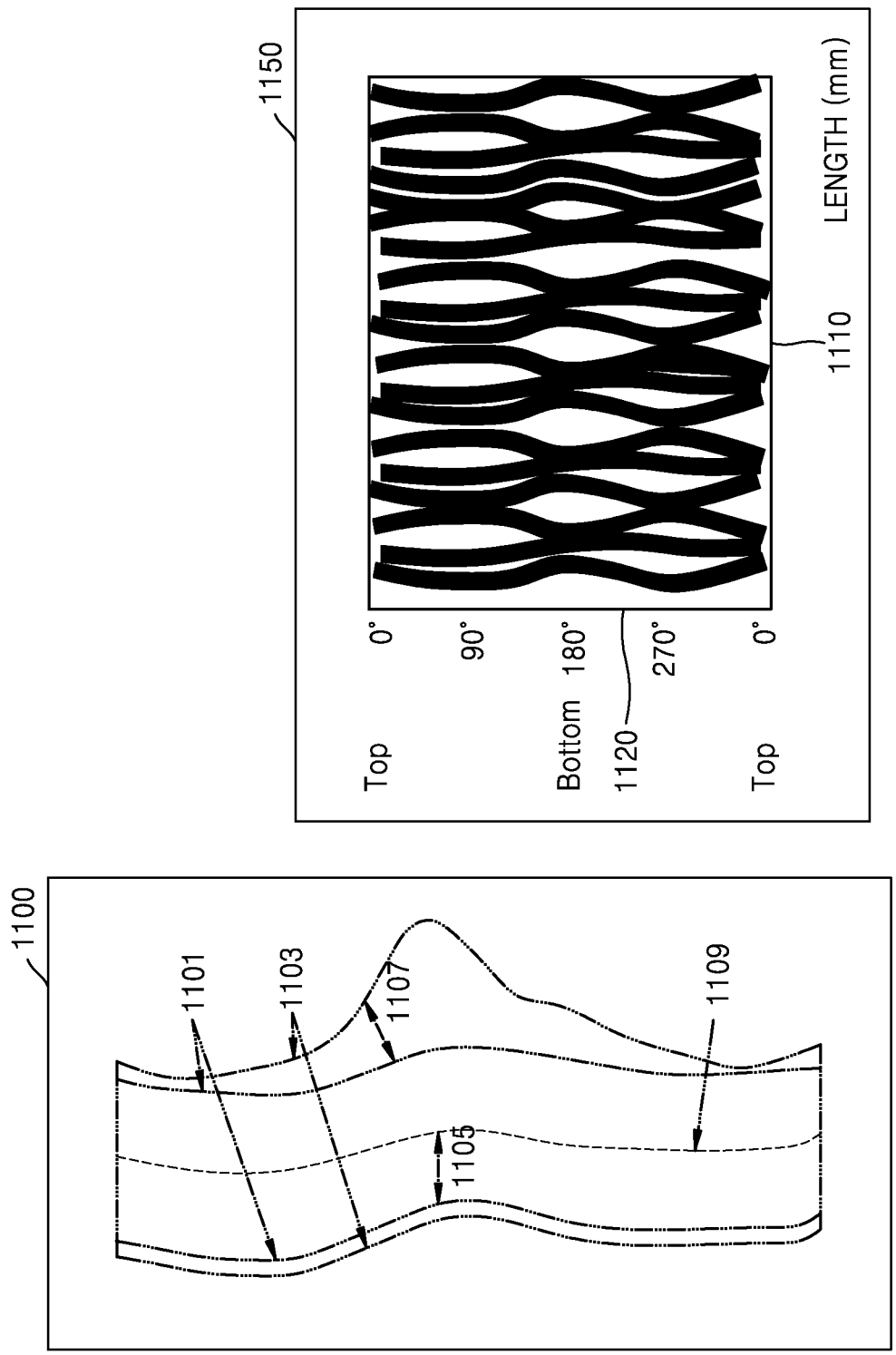
FIG. 11 is a diagram illustrating another example of a screen displaying a first ultrasound image and a second ultrasound image corresponding to an ROI, according to an exemplary embodiment.

FIG. 11 is a diagram illustrating another example of a screen displaying a first ultrasound image and a second ultrasound image corresponding to an ROI, according to an exemplary embodiment.

A first ultrasound image 1100 of FIG. 11 may correspond to the first ultrasound image 700 of FIG. 7. This has been described in detail with reference to FIG. 7, and thus, a detailed description is not provided.

A second ultrasound image 1150 may be an image that is shown when it is assumed that an inner wall of a blood vessel is seen while rotating by 0 degrees to 360 degrees about a center axis. That is, the second ultrasound image 1150 may be an image in which a surface of an inner wall is unfolded so as to be seen with the eyes.

In the second ultrasound image 1150, a characteristic of an inner wall may be imaged by using a color Doppler image so as to check an inner wall of an object at a glance. Also, the elasticity, a contrast agent augmentation characteristic, and a thickness of the inside of the object may be marked on the second ultrasound image 1150.

An abscissa axis 1110 of the second ultrasound image 1150 may indicate a position on a center line, and an ordinate axis 1120 of the second ultrasound image 1150 may indicate a rotation angle with respect to the center line. The ordinate axis 1120 may indicate 0 degrees to 360 degrees (illustrated as 0 degrees in FIG. 12). That is, a tubular shape is generated by connecting an image of an uppermost 0-degree portion and a lowermost 0-degree portion of the second ultrasound image 1150.

The second ultrasound image 1150 has been described as a plane corresponding to a surface of an inner wall, but is not limited thereto. The second ultrasound image 1150 may be a plane corresponding to a surface of an outer wall.

Moreover, both a surface of an inner wall and a surface of an outer wall may be marked on the second ultrasound image 1150. As an exemplary embodiment in which a surface of an inner wall and a surface of an outer wall are all marked, there are an exemplary embodiment, in which a surface of an inner wall and a surface of an outer wall are marked to overlap each other, and an exemplary embodiment in which a surface of an inner wall and a surface of an outer wall are marked in different regions. However, the inventive concept is not limited to the exemplary embodiments.

Figure 12:
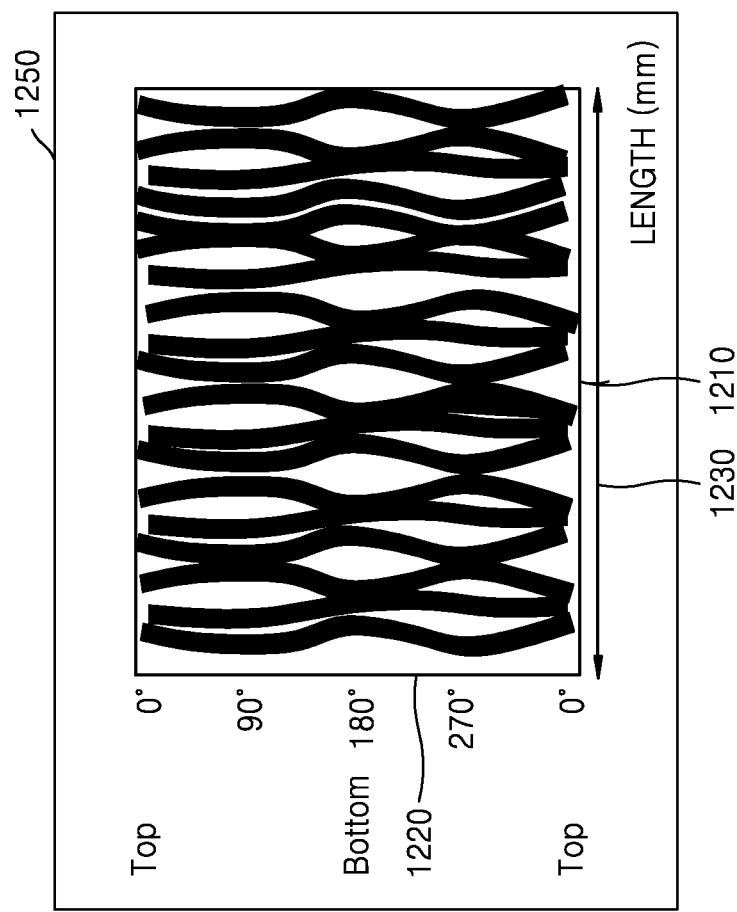
FIG. 12 is a diagram illustrating another example of a screen displaying a first ultrasound image and a second ultrasound image corresponding to an ROI, according to an exemplary embodiment.
Figure 12:
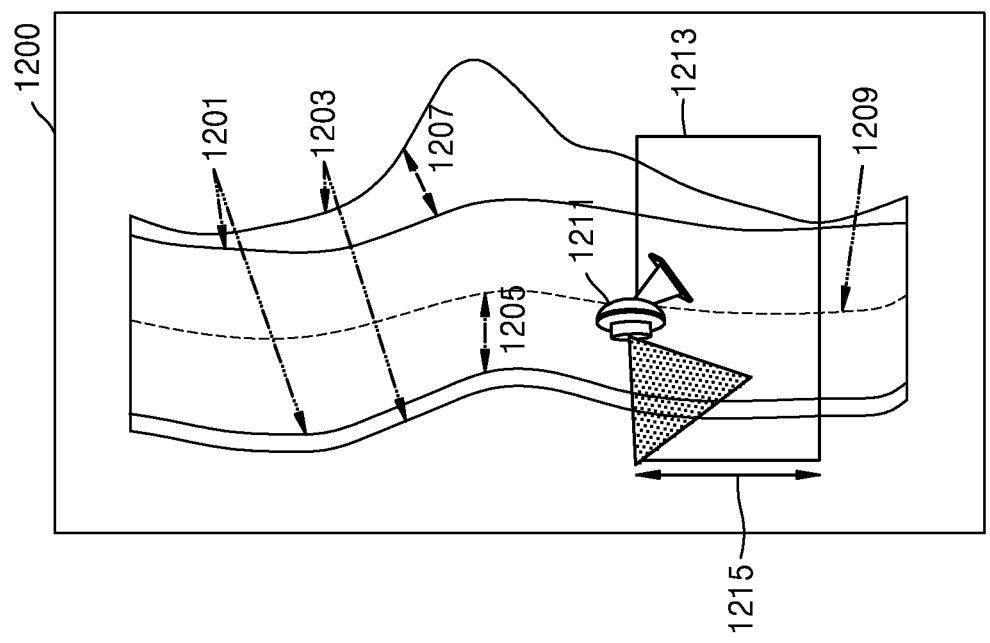

FIG. 12 is a diagram illustrating another example of a screen displaying a first ultrasound image and a second ultrasound image corresponding to an ROI, according to an exemplary embodiment.

Except that a cursor 1211 is positioned on a center line 1209, a first ultrasound image 1200 of FIG. 12 is the same as the first ultrasound image 1100 of FIG. 11, and thus, the same descriptions provided with regard to FIG. 11 are not repeated. The cursor 1211 may be moved along the center line 1209, based on a user input, and a user may move the cursor 1211 to an ROI 1213 to select the ROI 1213.

A second ultrasound image 1250 may be an image corresponding to the ROI 1213 which is selected by the cursor 1211 from an object included in the first ultrasound image 1200.

The user may designate a range 1230 of an abscissa axis 1210 of the second ultrasound image 1250 by using the cursor 1211. The abscissa axis 1210 may indicate a position on the center line 1209. Therefore, the range 1230 of the abscissa axis 1210 may correspond to a range 1215 which is marked in a center-line direction of the ROI 1213.

The user may designate the range 1230 of the abscissa axis 1210 of the second ultrasound image 1250 by using the cursor 1211. The abscissa axis 1210 may indicate a position on the center line 1209. Therefore, the range 1230 of the abscissa axis 1210 may correspond to the range 1215 which is marked in a center-line direction of the ROI 1213.

The user may limit a range of a horizontal axis and a range of a rotation angle by using the cursor 1211 which is illustrated in a camera shape. Also, the user may select and display at least one from among a plane corresponding to a surface of an inner wall and a plane corresponding to a surface of an outer wall in the second ultrasound image 1250.

According to the present embodiment, a surface of an inner wall and a surface of an outer wall are checked at a glance, and thus, the total time taken in diagnosing a surface of a wall of an object is reduced. Also, a position relationship between parts of a wall is checked at a time, and thus, an accuracy of a diagnosis is enhanced.

Figure 13:
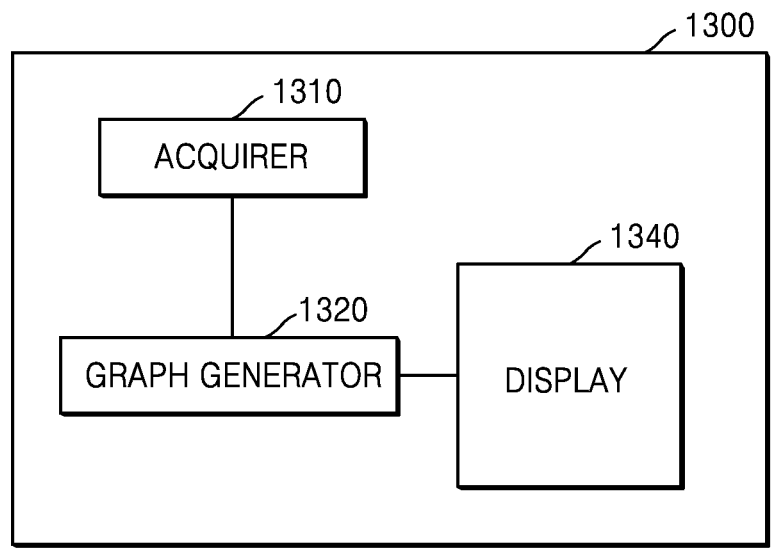
FIG. 13 is a block diagram illustrating a configuration of an ultrasound diagnostic apparatus according to an exemplary embodiment.

FIG. 13 is a block diagram illustrating a configuration of an ultrasound diagnostic apparatus 1300 according to an exemplary embodiment.

As illustrated in FIG. 13, the ultrasound diagnostic apparatus 1300 according to an exemplary embodiment may include an acquirer 1310, a graph generator 1320, and a display 1340.

The ultrasound diagnostic apparatus 1300 according to an exemplary embodiment illustrated in FIG. 13 is an ultrasound diagnostic apparatus for a tubular object which includes an inner wall and an outer wall.

The acquirer 1310 may acquire a center line which is formed in a long-axis direction of an object, based on ultrasound volume data of the object and acquire distance data which includes at least one selected from a distance from the center line to an inner wall and a distance from the center line to an outer wall.

The graph generator 1320 may generate an analysis graph, based on the center line and the distance data which are acquired by the acquirer 1310.

The display 1340 may display the analysis graph generated by the graph generator 1320. The display 1340 may correspond to the display 205 included in the ultrasound diagnostic apparatus 200 according to an exemplary embodiment illustrated in FIG. 2.

The ultrasound diagnostic apparatus 1300 of FIG. 13 may further include a controller (not shown). The controller may control an operation of the ultrasound diagnostic apparatus 1300. Also, the controller may control operations of the acquirer 1310, the graph generator 1320, and the display 1340. The controller may correspond to the controller 160 of FIG. 1.

Figure 14:
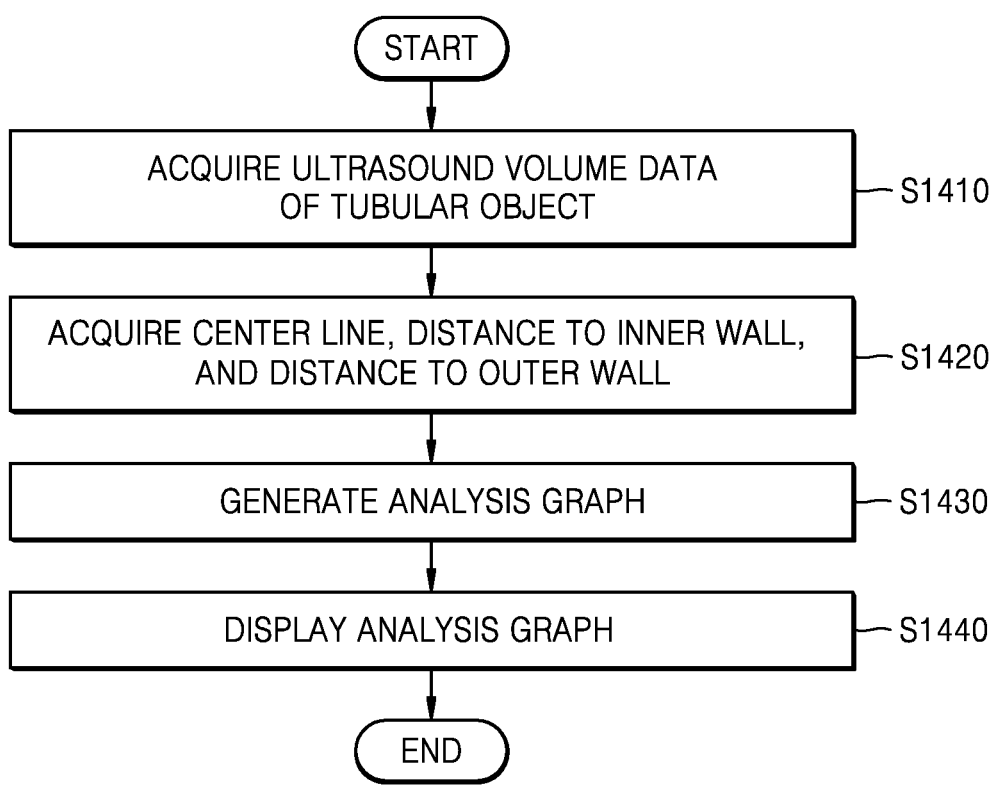
FIG. 14 is a flowchart for describing an ultrasound diagnostic method according to an exemplary embodiment.

FIG. 14 is a flowchart for describing an ultrasound diagnostic method according to an exemplary embodiment.

In operation S1410, the ultrasound diagnostic apparatus 1300 may acquire ultrasound volume data of an object.

In operation S1420, the acquirer 1310 may acquire a center line which is formed in a long-axis direction of the object. In operation S1420, the acquirer 1310 may acquire distance data which includes at least one selected from a distance from the center line to an inner wall and a distance from the center line to an outer wall.

In operation S1430, the graph generator 1320 may generate an analysis graph, based on the center line and the distance data which are acquired by the acquirer 1310.

In operation S1440, the display 1340 may display the analysis graph generated by the graph generator 1320. This will be described below in detail with reference to FIGS. 15 to 17.

Figure 15A:
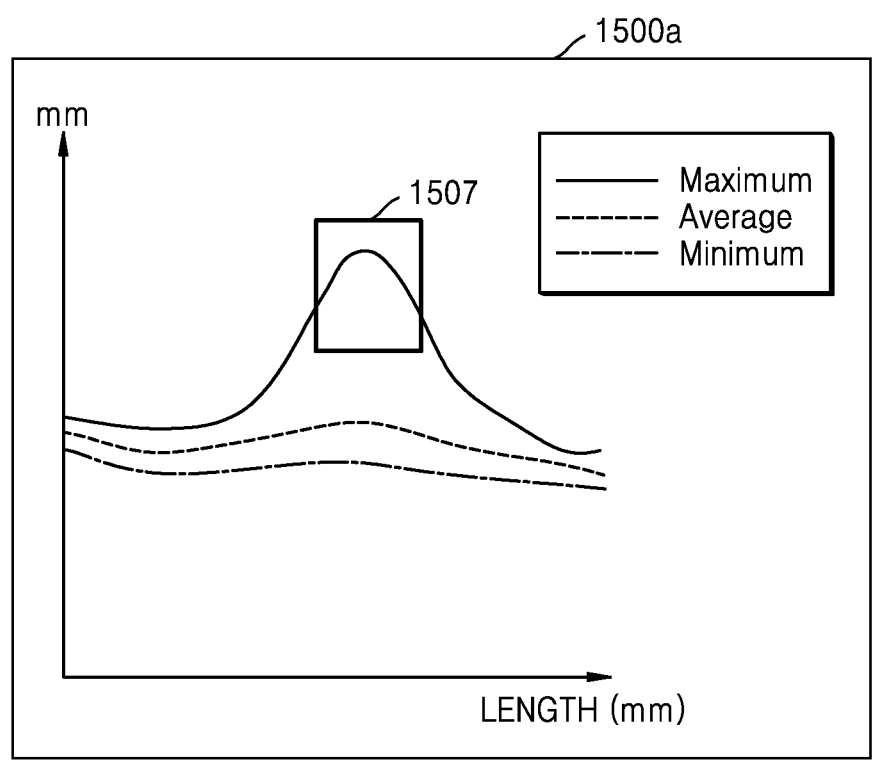
FIG. 15A is a diagram illustrating an example of a screen displaying an analysis graph, according to an exemplary embodiment.

FIG. 15A is a diagram illustrating an example of a screen displaying an analysis graph, according to an exemplary embodiment.

An analysis graph 1500 may correspond to the second ultrasound image 950 described above with reference to FIG. 9. Thus, the same descriptions provided with regard to FIG. 9 are not repeated.

An abscissa axis 1511 of the analysis graph 1500 may indicate a position on a center line of an object. An ordinate axis 1513 of the analysis graph 1500 may indicate a distance from the center line to an inner wall, a distance from the center line to an outer wall, and a thickness of the object.

The analysis graph may show a result which is obtained by calculating at least one selected from a maximum value 1501, a minimum value 1505, and an average value 1503 for at least one selected from i) the distance from the center line to the inner wall, ii) the distance from the center line to the outer wall, and iii) the thickness of the object.

The rapid changes in the distance from the center line to a surface of the outer wall or the inner wall and the thickness of the object are expected through a portion 1507, which is shown at the maximum value 1501 of the analysis graph 1500.

A range of the abscissa axis 1511 of the analysis graph 1500 may be adjusted according to a user input. Also, a kind of result data which is shown on the ordinate axis 1513 of the analysis graph 1500 may be adjusted according to a user input.

Figure 15B:
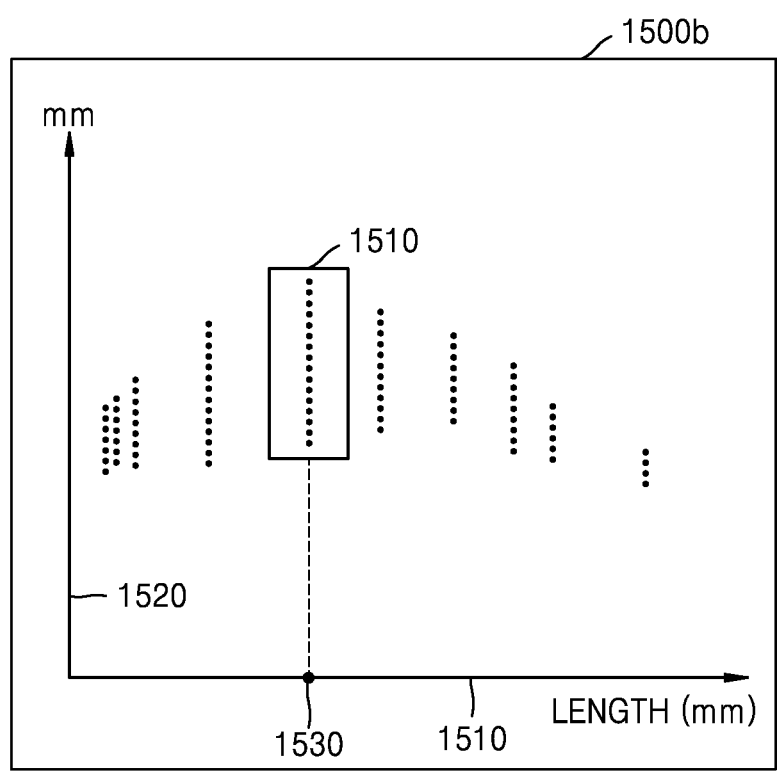
FIG. 15B is a diagram illustrating another example of a screen displaying an analysis graph, according to an exemplary embodiment.

FIG. 15B is a diagram illustrating another example of a screen displaying an analysis graph, according to an exemplary embodiment.

An analysis graph 1500b according to an exemplary embodiment may show a distribution of data which is acquired while rotating by 360 degrees along an inner wall or an outer wall with respect to a center line.

An abscissa axis 1510 of the analysis graph 1500b may indicate a position on the center line of an object. An ordinate axis 1520 of the analysis graph 1500b may indicate a distance from the center line to an inner wall, a distance from the center line to an outer wall, and a thickness of the object.

Data shown by the analysis graph 1500b includes at least one selected from the distance from the center line to the inner wall, the distance from the center line to the outer wall, and the thickness of the object.

A shape of an object in a part corresponding to a position 1530 on the center line may be expected through a data distribution 1510 of a part which is distributed over a widest range.

Figure 16:
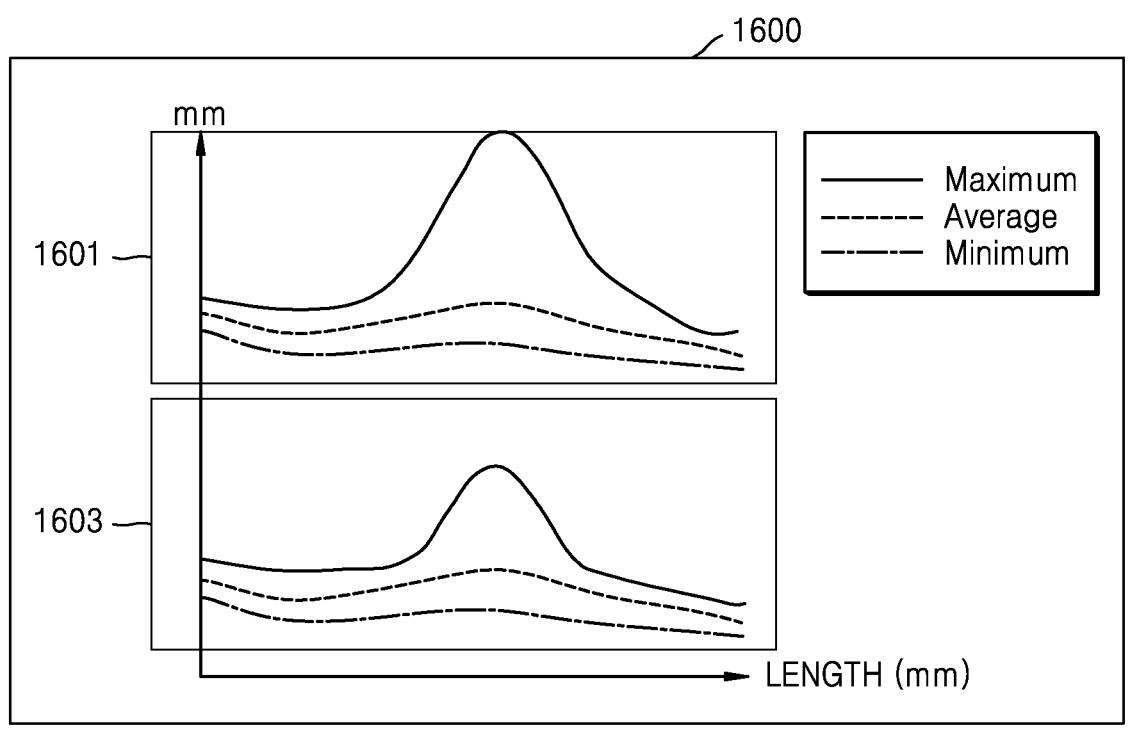
FIG. 16 is a diagram illustrating another example of a screen displaying an analysis graph, according to an exemplary embodiment.

FIG. 16 is a diagram illustrating another example of a screen displaying an analysis graph, according to an exemplary embodiment.

An analysis graph 1600 according to an exemplary embodiment may show various kinds of data at a time. An analysis graph 1601 for a minimum value, a maximum value, and an average value of a distance from a center line to an outer wall may be shown, and simultaneously, an analysis graph 1602 for a minimum value, a maximum value, and an average value of a thickness of an object may be shown.

In FIG. 16, an example where two kinds of data are shown on an analysis graph is illustrated, but the number of kinds of data is not limited.

Figure 17:
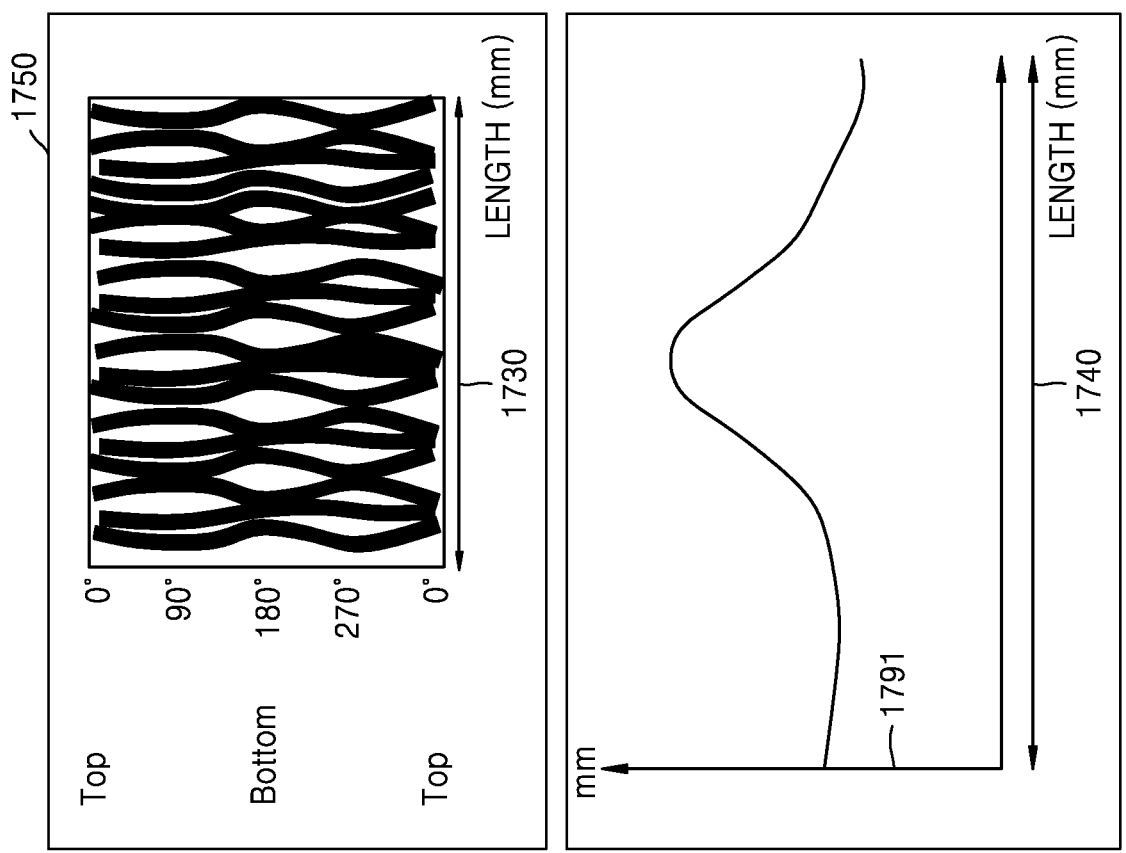
FIG. 17 is a diagram illustrating an example of a screen displaying an ultrasound image, according to an exemplary embodiment.
Figure 17:
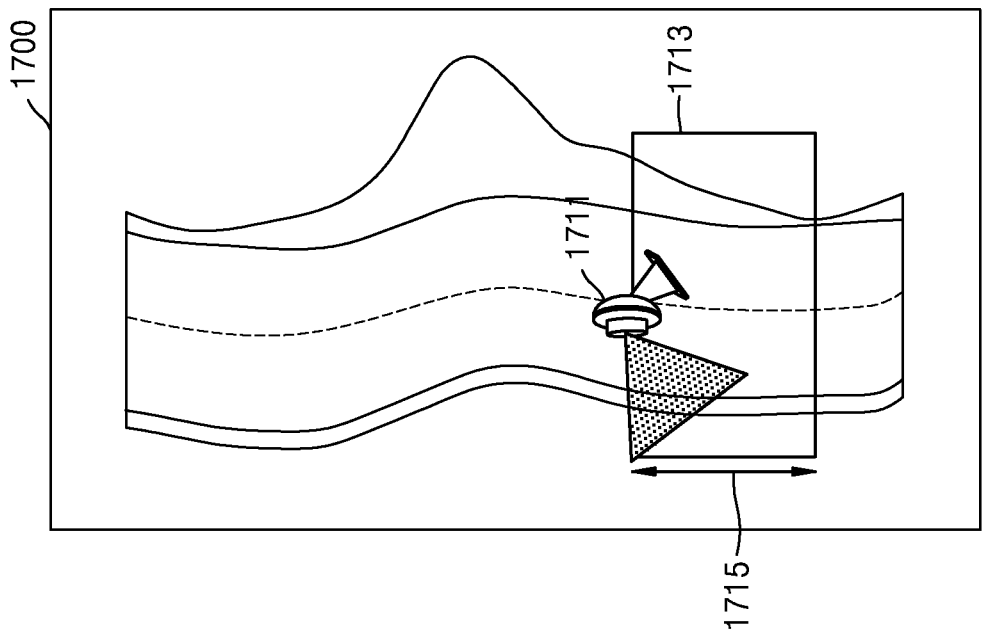

FIG. 17 is a diagram illustrating an example of a screen displaying an ultrasound image, according to an exemplary embodiment.

A first ultrasound image 1700 is an image which is displayed as a navigation view representing a center line of the inside of an object. The first ultrasound image 1700 is the same as the first ultrasound image 1000 of FIG. 10, and thus, the same descriptions provided with regard to FIG. 10 are not repeated. In the first ultrasound image 1700, a cursor 1711 positioned on the center line may be moved along the center line, and a user may move the cursor 1711 to an ROI 1713 to select the ROI 1713.

A second ultrasound image 1790 may be an analysis graph corresponding to the ROI 1713 which is selected by the cursor 1711 from the object included in the first ultrasound image 1700.

A third ultrasound image 1750 may be a plane image corresponding to a surface of an inner wall or an outer wall corresponding to the ROI 1713 which is selected by the cursor 1711 from the object included in the first ultrasound image 1700.

A user may designate a range 1740 of an abscissa axis of the second ultrasound image 1790 by using the cursor 1711. Simultaneously, a range 1730 of an abscissa axis of the third ultrasound image 1750 which is the plane image corresponding to the surface of the inner wall or the outer wall may be automatically selected. Also, the range 1730 of the abscissa axis of the third ultrasound image 1750 and a range 1740 of an abscissa axis of the analysis graph 1790 may be designated separately or simultaneously.

An abscissa axis may indicate a position on a center line. Therefore, the range 1730 of the abscissa axis of the third ultrasound image 1750 and the range 1740 of the abscissa axis of the analysis graph 1790 may correspond to a range 1715 which is marked in a center-line direction of the ROI 1713.

According to the present embodiment, the user may select, through only simple manipulation, the ROI 1713 of the object included in the first ultrasound image 1700 and check, through simple manipulation, which wall is thickened, thinned, or perforated, by using the analysis graph 1790. Also, a surface of an inner wall or an outer wall of a part which is to be diagnosed is checked at a glance.

As described above, according to the one or more of the above exemplary embodiments, a thickness of a wall of a tubular object and a wall of a circumference of a center line of the inside of the object are observed, and thus, a diagnosis is performed through only simple manipulation.

Moreover, according to the exemplary embodiments, a user manipulates an image displayed on a screen along a center line instead of an arbitrary point when diagnosing a tubular object. Also, the user intuitively knows a characteristic of an ROI, selected by the user, on a screen.

The ultrasonic diagnostic apparatus and the method of operating the same according to the exemplary embodiments may also be embodied as computer-readable codes on a computer-readable recording medium. The computer-readable recording medium is any data storage device that may store data which may be thereafter read by a computer system. Examples of the computer-readable recording medium include read-only memory (ROM), random-access memory (RAM), CD-ROMs, magnetic tapes, floppy disks, and optical data storage devices. The computer-readable recording medium may also be distributed over network-couple computer systems so that the computer-readable code may be stored and executed in a distributed fashion.

It should be understood that the exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A method for displaying an ultrasound image of an object having a tubular shape, the method comprising:
   acquiring ultrasound volume data of the object;
   generating a first ultrasound image which is obtained by imaging a surface of the object, based on the ultrasound volume data;
   generating a second ultrasound image which is obtained by imaging at least one selected from blood flow, stiffness, a thickness of a wall, and contrast agent augmentation of an inside of the object included in the first ultrasound image, based on the ultrasound volume data; and
   displaying the first ultrasound image and the second ultrasound image at the same time,
   wherein the first ultrasound image represents a slice that is parallel to an axis of the object and a center line of the object, and an abscissa axis of the second ultrasound image indicates a position on the center line.

2. The method of claim 1, wherein the generating of the second ultrasound image comprises generating at least one image which is selected from a color Doppler image, an elasticity image, and a contrast agent augmentation image of the inside of the object included in the first ultrasound image, based on the ultrasound volume data.

3. The method of claim 1, wherein the displaying comprises displaying the first ultrasound image in which the center line, which is formed in an axial direction of the object, is marked.

4. The method of claim 3, wherein the generating of the second ultrasound image comprises:
   acquiring distance data which includes at least one selected from a distance from the center line to an inner wall and a distance from the center line to an outer wall; and
   generating an analysis graph, as the second ultrasound image, based on the center line and the distance data.

5. The method of claim 4, wherein the displaying comprises:
   displaying the first ultrasound image on a first region of a screen; and
   displaying the second ultrasound image, corresponding to a region of interest (ROI) selected from the first ultrasound image, on a second region of the screen.

6. An ultrasound diagnostic apparatus for an object having a tubular shape, the ultrasound diagnostic apparatus comprising:
   a probe that transmits ultrasound waves to the object and receives ultrasound volume data from the object;
   a display; and
   a processor configured to:
   generate a first ultrasound image which is obtained by imaging a surface of the object, based on the ultrasound volume data;
   generate a second ultrasound image which is obtained by imaging at least one selected from blood flow, stiffness, a thickness of a wall, and contrast agent augmentation of an inside of the object included in the first ultrasound image, based on the ultrasound volume data; and
   control the display to display the first ultrasound image and the second ultrasound image,
   wherein the first ultrasound image represents a slice that is parallel to an axis of the object and a center line of the object and an abscissa axis of the second ultrasound image indicates a position on the center line.

7. The ultrasound diagnostic apparatus of claim 6, wherein the processor is configured to generates at least one image which is selected from a color Doppler image, an elasticity image, and a contrast agent augmentation image of the inside of the object included in the first ultrasound image, as the second ultrasound image, based on the ultrasound volume data.

8. The ultrasound diagnostic apparatus of claim 6, wherein the display displays the first ultrasound image in which the center line, which is formed in an axial direction of the object, is marked.

9. The ultrasound diagnostic apparatus of claim 8, wherein the processor is further configured to acquire distance data which includes at least one selected from a distance from the center line to an inner wall and a distance from the center line to an outer wall, and generates an analysis graph, as the second ultrasound image, based on the center line and the distance data.

10. The ultrasound diagnostic apparatus of claim 9, wherein the display displays the first ultrasound image on a first region of a screen, and displays the second ultrasound image, corresponding to a region of interest (ROI) selected from the first ultrasound image, on a second region of the screen.

11. The ultrasound diagnostic apparatus of claim 10, wherein the display configured to display a cursor, which is used to set the ROI, on the center line.

12. The ultrasound diagnostic apparatus of claim 11, wherein,
   the cursor is configured to be moved along the center line, and
   the second ultrasound image generator generates the analysis graph corresponding to the ROI which is set by the cursor, based on the ultrasound volume data.

* * * * *